US008501823B2

(12) United States Patent
Fujino et al.

(10) Patent No.: US 8,501,823 B2
(45) Date of Patent: Aug. 6, 2013

(54) OIL-IN-WATER EMULSION COSMETIC COMPOSITION AND METHOD FOR PRODUCING THE SAME

(75) Inventors: Jin Fujino, Kanagawa-ken (JP); Keiichi Ooyama, Kanagawa-ken (JP); Kazuhito Uchida, Mie-ken (JP); Yasuhiro Okubo, Mie-ken (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 235 days.

(21) Appl. No.: 12/573,667

(22) Filed: Oct. 5, 2009

(65) Prior Publication Data
US 2010/0022665 A1 Jan. 28, 2010

Related U.S. Application Data

(62) Division of application No. 10/580,575, filed as application No. PCT/JP2004/017459 on Nov. 25, 2004, now abandoned.

(30) Foreign Application Priority Data

Nov. 28, 2003 (JP) .................................. 2003-400590
Jun. 24, 2004 (JP) .................................. 2004-186841

(51) Int. Cl.
A61K 47/14 (2006.01)
(52) U.S. Cl.
USPC ......................................................... 514/785
(58) Field of Classification Search
None
See application file for complete search history.

(56) References Cited

U.S. PATENT DOCUMENTS

| 4,454,113 | A | 6/1984 | Hemker |
| 5,147,644 | A | 9/1992 | Oppenlaender et al. |
| 5,397,497 | A | 3/1995 | Jakobson et al. |
| 6,506,391 | B1 * | 1/2003 | Biatry ........................... 424/401 |
| 2004/0115161 | A1 | 6/2004 | Oyama |
| 2006/0286133 | A1 | 12/2006 | Fujino et al. |

FOREIGN PATENT DOCUMENTS

| CN | 1278704 A | 1/2001 |
| EP | 0 138 0278 | 1/2004 |
| EP | 1 623 694 A1 | 2/2006 |
| JP | 58-185537 | 10/1983 |
| JP | 62-250941 A | 10/1987 |
| JP | 01-176446 | 7/1989 |
| JP | 02-172938 | 7/1990 |
| JP | 05-310625 | 11/1993 |
| JP | 06-157289 A | 6/1994 |
| JP | 07-100355 | 4/1995 |
| JP | 07-173380 A | 7/1995 |
| JP | 07-185294 A * | 7/1995 |
| JP | 07-187947 | 7/1995 |
| JP | 07-308560 | 11/1995 |
| JP | 08-143513 | 6/1996 |
| JP | 09-208444 | 8/1997 |
| JP | 11-152205 | 6/1999 |
| JP | 11-262653 A * | 9/1999 |
| JP | 2003-055128 A | 2/2003 |
| JP | A 2004-035420 | 2/2004 |
| JP | 2004-256514 | 9/2004 |
| WO | WO 99/20111 | 4/1999 |
| WO | WO 02/078650 | 10/2002 |

OTHER PUBLICATIONS

Streitweiser et al. in Introduction to Organic Chemistry, pp. 509-510, 3rd Edition, Macmillan, 1985.*
Polyglycerols—General Overview in http://www.solvaypolyglycerol.com/docroot/glycerol/static_files/attachments/polyglycerols_general_overview.pdf.*
PolyglycerinePolyglycerol in www.chemblink.com/products/25618-55-7.htm.*
International Search Report from PCT priority application Serial No. PCT/JP2004/006469.
Written Opinion from PCT priority application No. PCT/JP2004/006469.
An Office Action issued in counterpart Japanese Patent Application No. 2004-186841, dated Jun. 30, 2009.
The European Search Report issued in corresponding European Patent Application No. 04819389, dated Jun. 29, 2009.
Database WPI Week 198934, Thomson Scientific, London, GB; AN 1989-244471 XP002533007 (Corresponds to Reference No. 4).
Database WPI Week 200467, Thomson Scientific, London, GB; AN 2004-680317 XP002533008 (Corresponds to Reference No. 5).
English translation of the Office Action for Chinese Patent Application No. 200480012310X, dated Jun. 8, 2007.
Office Action for Chinese Patent Application No. 200480012310X, dated Jun. 8, 2007.
*Petrochemistry*. 30(1):38-43 (1981).
Streitwieser et al., "Introduction to Organic Chemistry," Third Edition, Macmillan Publishing Company, pp. 509-510, 1985.
International Search Report from PCT priority application Serial No. PCT/JP2004/006469, dated Sep. 7, 2004.
Written Opinion from PCT priority application Serial No. PCT/JP2004/006469, dated Sep. 7, 2004.

* cited by examiner

*Primary Examiner* — Dennis Heyer
(74) *Attorney, Agent, or Firm* — Knobbe Martens Olson & Bear LLP

(57) ABSTRACT

To provide an oil-in-water emulsion cosmetic composition obtained by using a polyglycerin fatty acid ester as a surfactant, which has high stability against temperature and is excellent in tactile sensation, and a method for producing the same, the present invention provides an oil-in-water emulsion cosmetic composition, wherein the composition comprises 1) a polyglycerin fatty acid ester, as a surfactant, having a hydroxyl value of 450 to 700, a fatty acid residue having 16 to 18 carbon atoms accounting for 50 to 100% by mass of all constituent fatty acid residues, the polymerization degree of glycerin having specific distribution, 2) an oily component, and 3) water.

2 Claims, No Drawings

OIL-IN-WATER EMULSION COSMETIC COMPOSITION AND METHOD FOR PRODUCING THE SAME

RELATED APPLICATIONS

This application is a divisional of U.S. patent application Ser. No. 10/580,575, filed on May 25, 2006, now abandoned which is the U.S. National Phase filing under 35 U.S.C. §371 of PCT/JP2004/017459, filed Nov. 25, 2004, which designated the United States and was published in a language other than English, which claims priority under 35 U.S.C. §119(a)-(d) to Japanese patent application Nos. 2003-400590, filed Nov. 28, 2003 and 2004-186841, filed Jun. 24, 2004. The content of these applications is incorporated herein by reference in their entireties.

TECHNICAL FIELD

The present invention relates to an oil-in-water emulsion cosmetic composition comprising, as components, 1) a polyglycerin fatty acid ester as a surfactant (or an emulsifier), 2) an oily component, and 3) water, and a method for producing the same and, more particularly, to an oil-in-water emulsion cosmetic composition obtained by using a polyglycerin fatty acid ester, which is excellent in emulsion stability such as stability under various temperature conditions (hereinafter referred to as "stability against temperature") and is also excellent in tactile sensation, and a method for producing the same.

BACKGROUND ART

In oil-in-water emulsion cosmetic compositions such as ointment, cream, milky lotion and serum, a polyoxyethylene-based surfactant has been used. Examples of the polyoxyethylene-based surfactant include polyoxyethylene sorbitan fatty acid esters, polyethylene glycol fatty acid esters and polyoxyethylene alkyl ethers.

These polyoxyethylene-based surfactants are used because these surfactants have various HLB values and therefore it becomes possible to widely adjust the HLB value by using them in combination, resulting in wide applications of the surfactant.

However, it has been known that this polyoxyethylene-based surfactant has some fear for safety to the human body and high concentration of the polyoxyethylene-based surfactant causes irritation of the skin. Hydrophilicity and lipophilicity of the polyoxyethylene-based surfactant easily vary with the temperature and an oil-in-water emulsion cosmetic composition obtained by using the same deteriorates by temperature variation.

As a surfactant which is excellent in safety as compared with a polyoxyethylene-based surfactant and is free from discomfort of flavor or odor, for example, a polyglycerin fatty acid ester used widely in foods has recently been used in a cosmetic composition (Japanese Unexamined Patent Publication, First Publication No. Sho 58-185537). It has commonly been known that hydrophilicity and lipophilicity of the polyglycerin fatty acid ester hardly vary with temperature variation and thus an oil-in-water emulsion cosmetic composition obtained by using the same is also stable against temperature variation.

It is considered that various stabilities of the oil-in-water emulsion cosmetic composition depend on stability in an emulsified (state) (hereinafter referred to as "emulsion stability") of a cosmetic composition.

To the contrary, when an oil-in-water emulsion cosmetic composition having poor emulsion stability is exposed under severe conditions during a circulation process or use by a consumer, there arises a problem that thickening, solidification, separation and aggregation may occur and thus commercial value may be lost. There also arises a problem that an emulsion cosmetic composition is thickened or solidified by temperature variation during storage of the product or shaking during transportation, thus resulting in separation and aggregation.

As described above, the oil-in-water emulsion cosmetic composition obtained by using the polyglycerin fatty acid ester had a problem how emulsion stability is enhanced.

To enhance emulsion stability, an approach of improving the surfactant of the oil-in-water emulsion cosmetic composition and an approach of improving the emulsification method of the oil-in-water emulsion cosmetic composition have been made and various emulsification methods have been developed.

An emulsification method, which has been employed most popularly, is a method in which an oil phase containing a surfactant is added in an aqueous phase and the oil phase is emulsified by a mechanical shear force of an emulsifying machine such as homomixer (hereinafter referred to as a "dispersion emulsification method"). However, according to this method, the functions of the surfactant do not efficiently exert on interface between oil and water. With the increase of the level of quality required to cosmetics, various formulations in a cosmetic composition have been developed and it becomes difficult to decrease the particle size of emulsified particles. There is a limit in the development of the emulsifying machine, and the development of a new emulsification method was made. Therefore, a phase inversion emulsification method (reverse emulsification method) was developed as the emulsification method using a surface chemical technique, not a technique due to a mechanical force.

The phase inversion emulsification method is an emulsification method which requires to match a HLB value of the surfactant to be added to a required HLB value of an oily component, and is specifically a method comprising dissolving or dispersing a surfactant having almost the same HLB value as the required HLB value of an oily component in the oily phase, adding an aqueous phase to obtain a water-in-oil emulsion cosmetic composition (W/O emulsion cosmetic composition), and adding furthermore an aqueous phase thereby to convert into an oil-in-water (O/W) emulsion cosmetic composition through phase inversion, thus obtaining an oil-in-water emulsion cosmetic composition (O/W emulsion cosmetic composition). In the phase inversion emulsification method, a mixture of two or more kinds of surfactants is commonly used.

When the phase inversion emulsification method is used, it is possible to obtain an oil-in-water emulsion cosmetic composition having a small emulsified particle size as compared with a dispersion emulsification method in which an oil phase is added to an aqueous phase to produce an oil-in-water emulsion cosmetic composition. Therefore, it is commonly used in the production of a cosmetic composition.

It is reported that the oil-in-water emulsion cosmetic composition having a small emulsified particle size can be obtained by the following reason. That is, when the required HLB value of the oily component and the HLB value of the surfactant are adjusted to almost the same value, emulsified particles are produced via a lamellar liquid crystal phase in case of phase inversion (see 1981, "Petrochemistry", Vol. 30, No. 1, pp. 38-43). As a detailed mechanism, it is made clear that submicron-sized emulsified particles are produced through the following steps: W/O emulsion cosmetic composition→lamellar liquid crystal phase→O (oil phase)/D (surfactant phase)→O/W emulsion cosmetic composition in the process of adding an aqueous phase to an oil phase (see 1981, "Petrochemistry", Vol. 30, No. 1, pp. 38-43).

Examples of the emulsification method employing a surface chemical technique include, in addition to this phase inversion emulsification method, an emulsification method employing a surface chemical technique, such as D phase emulsification method or liquid crystal emulsification method. However, in the emulsification method employing a surface chemical technique, for example, a polyhydric alcohol must be added as an essential component in case of emulsification. Therefore, the product is sensorily restricted, that is, appearance and formulation are restricted and it requires it takes a long time to previously study due to a phase diagram. With respect to load in the production, there were drawbacks that a cosmetic composition can not be produced according to the formulation in which a polyhydric alcohol gel must be produced and long time is required to emulsify, and also it is impossible to add in the amount enough to uniformly disperse by an agitator an oil phase before emulsification and a polyhydric alcohol, that is, the formulation in which the oil phase and polyhydric alcohol are contained in a small amount.

Therefore, there is proposed a method of decreasing the particle size of emulsified particles, without adding the essential components or taking long time in case of emulsification, by adopting a surface chemical technique employing the above-described phase inversion emulsification step in the dispersion emulsification method in which an aqueous phase is added to an oil phase and emulsification is conducted by a mechanical force, that is, a dispersion emulsification method employing self-emulsification (hereinafter referred to as a "self-emulsification method"). This method is a method, in which, when an oily component containing a surfactant having self emulsification characteristics added therein is contacted with water, self-emulsification based on the step of the phase inversion emulsification rapidly occurs and an oil-in-water emulsion cosmetic composition having a small emulsified particle size can be produced. The oil-in-water emulsion cosmetic composition obtained by using such a self-emulsification method has an advantage that it can overcome defects in the development process or production and is excellent in commodity.

It is generally known that such an emulsification method employing self emulsification characteristics of the surfactant can be applied in a polyoxyethylene-based surfactant. However, in this case, it is necessary to add a polyoxyethylene-based surfactant in a large amount of 100 to 120% by mass based on 100% by mass of the oily component so as to rapidly cause self-emulsification when contacted with water. However, it has been known that this polyoxyethylene-based surfactant has some fear for safety to the human body and high concentration of the polyoxyethylene-based surfactant causes irritation of the skin, as described above. The oil-in-water emulsion cosmetic composition obtained by this method using this polyoxyethylene-based surfactant has a drawback such as poor tactile sensation.

As a method of emulsifying an oil-in-water emulsion cosmetic composition obtained by using the polyglycerin fatty acid ester, for example, a D phase emulsification method and a liquid crystal emulsification method have recently been used, in addition to a conventional dispersion emulsification method, and also a phase inversion emulsification method, which could have not been used, has recently been used.

However, the method except for these dispersion emulsification methods has a problem such as restriction of the product and a problem in the production.

To the contrary, when the self-emulsification method is applied to an oil-in-water emulsion cosmetic composition obtained by using a polyglycerin fatty acid ester, a polyglycerin fatty acid ester is not easily dissolved in an oily component, and if it is dissolved in the oily component, the composition is not self-emulsified and is emulsified only by a mechanical force in a homomixer. Therefore, the resulting oil-in-water emulsion cosmetic composition had poor emulsion stability. Therefore, the oil-in-water emulsion cosmetic composition produced by the dispersion emulsification method employing self-emulsification using a polyglycerin fatty acid ester was not circulated in the market. The diglycerin monofatty acid ester having self emulsification characteristics is circulated but has poor self emulsification characteristics, and thus a satisfactory emulsion has never been obtained.

DISCLOSURE OF THE INVENTION

An object to be achieved by the present invention is to provide an oil-in-water emulsion cosmetic composition obtained by using a polyglycerin fatty acid ester as a surfactant, which has high stability against temperature and is excellent in tactile sensation, and a method for producing the same. The stability against temperature in the present invention refers to high temperature stability, low temperature stability, stability against temperature variation, and stability against high temperature shaking.

The present inventors have intensively studied and found that the above object can be achieved by an oil-in-water emulsion cosmetic composition comprising 1) a polyglycerin fatty acid ester, as a surfactant, having a hydroxyl value of 450 to 700, a fatty acid residue having 16 to 18 carbon atoms accounting for 50 to 100% by mass of all constituent fatty acid residues, and a polymerization degree of glycerin having specific distribution, 2) an oily component, and 3) water, and thus completing the following oil-in-water emulsion cosmetic compositions and production methods.

[1] An oil-in-water emulsion cosmetic composition,
wherein the oil-in-water emulsion cosmetic composition comprises:
a component A: a polyglycerin fatty acid ester having a hydroxyl value of 450 to 700, a fatty acid residue having 16 to 18 carbon atoms accounting for 50 to 100% by mass of all constituent fatty acid residues, the total content of a dimer and a trimer of a cyclic polyglycerin being from 0 to 3% by mass, the total content of an undecamer or multimer of polyglycerin being from 10 to 30% by mass, and the each content of a tetramer to a decamer of polyglycerin being from 4 to 20% by mass, based on 100% by mass of polyglycerin constituting the polyglycerin fatty acid ester,
a component B: an oily component, and
a component C: water, and
the amount of the component A is from 0.001 to 25% by mass, the amount of the component B is from 0.001 to 60% by mass, and the amount of the component C is from 10 to 99% by mass.

[2] The oil-in-water emulsion cosmetic composition according to [1], wherein the amount of the component A is from 0.01 to 15% by mass, the amount of the component B is from 0.01 to 50% by mass, and the amount of the component C is from 30 to 95% by mass.

[3] The oil-in-water emulsion cosmetic composition according to [1], wherein a hydroxyl value of the polyglycerin fatty acid ester as the component A is from 550 to 700, at least one of a polyhydric alcohol fatty acid ester having a hydroxyl value of 100 to 500 (excluding component A) and a polyhydric alcohol alkyl ether having a hydroxyl value of 100 to 500 is added as a component D, and the amount of the component D is from 1 to 100% by mass based on the amount of the component A.

[4] The oil-in-water emulsion cosmetic composition according to [3], wherein the amount of the component A is from 0.01 to 15% by mass, the amount of the component B is from 0.01 to 50% by mass, the amount of the component C is from 30 to 95% by mass, and the amount of the component D is from 1 to 100% by mass based on the amount of the component A.

[5] The oil-in-water emulsion cosmetic composition according to [1], wherein the fatty acid residue having 16 to 18 carbon atoms as the component A is at least one selected from isostearic acid residue, oleic acid residue, palmitic acid residue and stearic acid residue.

[6] The oil-in-water emulsion cosmetic composition according to [1], further comprising a thickener.

[7] The oil-in-water emulsion cosmetic composition according to [1], wherein the oil-in-water emulsion cosmetic composition is at least one selected from cream in general and milky lotion, sun tan cream, sun-block cream, shaving cream, cleansing cream, facial cleansing cream, lotion in general, sun tan lotion, sun-block lotion, shaving lotion, serum, lipstick, gel, cleansing gel, moisture gel, pack, emulsion foundation, emulsified eye shadow, nail treatment, shampoo, conditioner, and hair treatment.

[8] A method for producing the oil-in-water emulsion cosmetic composition according to [1], wherein the method comprises the step of adding an oil phase containing the component A and the component B to an aqueous phase containing a component C and emulsifying them.

[9] The method for producing the oil-in-water emulsion cosmetic composition according to [8], wherein the emulsification temperature is from 10 to 90° C.

[10] A method for producing the oil-in-water emulsion cosmetic composition according to [3], wherein the method comprises the step of adding an oil phase containing a component A, a component B and a component D to an aqueous phase containing a component C and emulsifying them.

[11] The method for producing the oil-in-water emulsion cosmetic composition according to [10], wherein the emulsification temperature is from 10 to 90° C.

The oil-in-water emulsion cosmetic composition of the present invention is excellent in emulsion stability, that is, stability against temperature such as 1) high temperature stability (for example, emulsion stability at 50° C.), 2) low temperature stability, 3) stability against temperature variation, or 4) stability against high temperature shaking, and is also excellent in tactile sensation. That is, the oil-in-water emulsion cosmetic composition of the present invention exerts the following effects: 1) texture in appearance, 2) free from greasy feel when applied to the skin, 3) excellent transparent feel, and 4) good compatibility (rapidly compatible with skin).

According to the method for producing an oil-in-water emulsion cosmetic composition of the present invention, an oil-in-water emulsion cosmetic composition capable of exerting the above effects can be produced.

BEST MODE FOR CARRYING OUT THE INVENTION

First, the component A will be described.

The hydroxyl value of the polyglycerin fatty acid ester used in the present invention is from 450 to 700, preferably from 550 to 700, more preferably from 500 to 650, and particularly preferably from 550 to 650. When the hydroxyl value is less than 450, the resulting oil-in-water emulsion cosmetic composition has poor emulsion stability because of poor self-emulsifiability. On the other hand, when the hydroxyl value is more than 700, the polyglycerin fatty acid ester is not dissolved in an oily component and an oil-in-water emulsion cosmetic composition can not be produced.

When the hydroxyl value of the polyglycerin fatty acid ester is from 550 to 700, it is preferred to add together with a component D described hereinafter. Emulsion stability and stability against temperature of the resulting oil-in-water emulsion cosmetic composition can be more improved by adjusting the hydroxyl value of the component A within a range from 550 to 700 and adding the component D.

The hydroxyl value described in the present invention can be measured by determining the amount (mg) of potassium hydroxide which is required to neutralize acetic acid required to acetylate free hydroxyl groups contained in 1 g of a sample according to Standard Methods for the Analysis of Fats, Oils and Related Materials.

The content of the fatty acid residue having 16 to 18 carbon atoms contained in the polyglycerin fatty acid ester as the component A is from 50 to 100% by mass, preferably from 55 to 100% by mass, and particularly preferably from 60 to 100% by mass, based on 100% by mass of all constituent fatty acid residues. When the content of the fatty acid residue having 16 to 18 carbon atoms is less than 50% by mass, the resulting oil-in-water emulsion cosmetic composition has poor emulsion stability and also texture and transparency become inferior.

The fatty acid residue may be either a linear fatty acid residue or a branched fatty acid residue. The linear fatty acid residue may be either a linear saturated fatty acid residue or a linear unsaturated fatty acid residue.

The branched fatty acid residue may be either a branched saturated fatty acid residue or a branched unsaturated fatty acid residue, but is preferably a branched saturated fatty acid residue taking account of availability of the material of the fatty acid in the production of the polyglycerin fatty acid ester.

Examples of the linear saturated fatty acid residue having 16 to 18 carbon atoms include a palmitic acid residue, a margaric acid residue and a stearic acid residue, and a palmitic acid residue and a stearic acid residue are particularly preferable.

Examples of the linear unsaturated fatty acid residue having 16 to 18 carbon atoms include unsaturated monohydroxy acid residues such as an oleic acid residue, a palmitoleic acid residue and a ricinoleic acid residue, and an oleic acid residue is preferable. A mixed fatty acid residue derived from palm oil containing 50% by mass or more of an oleic acid residue is included therein.

Examples of the branched fatty acid residue having 16 to 18 carbon atoms include an isostearic acid residue (for example, 16-methylheptadecanoyl group, 15-methylheptadecanoyl group, 10-methylheptadecanoyl group and poly-branched isostearic acid residue) and an isopalmitic acid residue (for example, 14-methylpentadecanoyl group), and an isostearic acid residue is preferable and a 16-methylheptadecanoyl group is more preferable.

It is necessary that the total content of a dimer and a trimer of a cyclic polyglycerin in a polyglycerin constituting a polyglycerin fatty acid ester as the component A is from 0 to 3% by mass, preferably from 0 to 2% by mass, and particularly preferably from 0 to 1% by mass. When the content of the dimer and the trimer of the cyclic polyglycerin is more than 3% by mass, the resulting oil-in-water emulsion cosmetic composition has poor emulsion stability and thus separation occurs during the storage.

The dimer or trimer of the polyglycerin may include, in addition to a cyclic compound, a noncyclic compound and those having both a cyclic moiety and a noncyclic moiety.

It is necessary that the total content of an undecamer or a multimer of a polyglycerin in a polyglycerin constituting a polyglycerin fatty acid ester as the component A is from 10 to 30% by mass, preferably from 12 to 28% by mass, and more preferably from 15 to 26% by mass. When the content is not within a range from 10 to 30% by mass, the resulting oil-in-water emulsion cosmetic composition has poor emulsion stability, and therefore it is not undesirable.

Furthermore, the each content of a tetramer to decamer polyglycerin in a polyglycerin constituting a polyglycerin fatty acid ester as the component A is from 4 to 20% by mass, preferably from 4 to 15% by mass, and particularly preferably from 4 to 12% by mass. Because, when each content of the tetramer to decamer polyglycerin is not within a range from 4 to 20% by mass, the resulting oil-in-water emulsion cosmetic composition has poor emulsion stability and thus separation occurs during the storage.

The polyglycerin constituting the polyglycerin fatty acid ester as the component A may contain a glycerin (monomer).

The composition of the polyglycerin is determined by the method converting a polyglycerin into a polyglycerin derivative and performing separation determination of the polyglycerin derivative using a GC method (gas chromatography). Analysis by the GC method can be easily carried out by temperature-rising analysis in a range from 100 to 250° C. with a rising rate of 10° C./min. using a fused silica capillary tube in which a low polar liquid phase such as methyl silicone is chemically bonded.

The composition can be easily determined by the method of introducing a gas chromatograph into a double focusing mass spectrograph, ionizing through chemical ionization, followed by the measurement, determination of a molecular weight of a peak on the gas chromatogram from the molecular weight of parent ions and further determination of the polymerization degree of a glycerin from the chemical formula, but the method is not limited to these methods.

The content of the polyglycerin constituting the polyglycerin fatty acid ester as the component A may be within the above range and the polyglycerin may be produced by a dehydration condensation method or a synthesis and purification method using known epichlorohydrin or glycidol as a starting material, and a commercially available product can also be used. Examples of the commercially available product include products (for example, Great Oil D-10, Great Oil D-11 and Great Oil D-12) manufactured by Taiyo Kagaku Co., Ltd.

The polyglycerin fatty acid ester as the component A of the present invention can be produced by employing a known method for producing a polyglycerin fatty acid ester and specifying the above-described material to be charged.

For example, the polyglycerin fatty acid ester can be obtained by charging a specific polyglycerin, that is, a polyglycerin in which, based on 100% by mass of the polyglycerin, the total content of a dimer and a trimer of a cyclic polyglycerin is from 0 to 3% by mass, the total content of an undecamer or a multimer of a polyglycerin is from 10 to 30% by mass, and the each content of a tetramer to a decamer of a polyglycerin is from 4 to 20% by mass (for example, a product Great Oil D-10 manufactured by Taiyo Kagaku Co., Ltd.), a fatty acid having 16 to 18 carbon atoms and a catalyst in a reaction vessel and esterifying while heating within a range from 200 to 250° C. under stirring in a nitrogen gas flow.

The hydroxyl value of the component A can be adjusted by a ratio of the polyglycerin and the fatty acid.

The component B will now be described.

The component B to be used in the present invention may be any one which is an oily component used in a cosmetic composition. Examples of the oily component include animal and vegetable fats and oils, semisynthetic fats and oils, hydrocarbon oil, higher fatty acid, ester oil, silicone oil, fat-soluble vitamin, saturated linear alcohol and linear monoalkyl glyceryl ether, and these oily components may be used alone or in combination.

Specific examples of the component B used in the present invention include, but are not limited to, the followings and these oily components may be used alone or in combination.

Examples of animal and vegetable fats and oils and semisynthetic fats and oils include avocado oil, linseed oil, almond oil, olive oil, carnauba wax, candelilla wax, beef tallow, beef leg fat, beef bone fat, hardened beef tallow, wheat germ oil, sesame oil, rice germ oil, rice bran oil, safflower oil, soybean oil, camellia oil, evening primrose oil, corn oil, rapeseed oil, horse fat, palm oil, palm kernel oil, castor oil, hardened castor oil, sunflower oil, jojoba oil, macadamia nuts oil, beeswax, mink oil, cotton seed oil, coconut oil, hardened coconut oil, peanut oil, lanolin, liquid lanolin, reduced lanoline and lanolin fatty acid isopropyl.

Examples of the hydrocarbon oil include squalane, olive squalane, squalene, ceresin, paraffin, paraffin wax, liquid paraffin, microcrystalline wax, petrolatum and α-olefin oligomer. Examples of the commercially available product of liquid paraffin include products (CARNATION®) manufactured by Witco Chemical Corporation.

Examples of the higher fatty acid include lauric acid, myristic acid, palmitic acid, stearic acid, behenic acid, undecylenic acid, oleic acid, linoleic acid, linolenic acid, isostearic acid and 12-hydroxystearic acid.

Examples of the ester oil include diisobutyl adipate, 2-hexyldecyl adipate, isononyl isononanate, isotridecyl isononanate, isostearyl myristate, di-2-heptylundecyl adipate, isostearyl isostearate, trimethylolpropane triisostearate, cetyl 2-ethylhexanoate, neopentyl glycol di-2-ethylhexanoate, trimethylolpropane tri-2-ethylhexanoate, pentaerythritol tetra-2-ethylhexanoate, cetyl octanoate, oleyl oleate, octyldodecyl oleate, decyl oleate, neopentyl glycol dicaprate, 2-ethylhexyl succinate, isocetyl stearate, butyl stearate, diisopropyl sebacate, cetyl lactate, myristyl lactate, 2-ethylhexyl palmitate, 2-hexyldecyl palmitate, 2-heptylundecyl palmitate, cholesteryl 12-hydroxystearate, phytosteryl oleate, diisostearyl malate, paramethoxycinnamate ester, 2-ethylhexyl paramethoxycinnamate, pentaerythrite tetrarosinate, glyceryl triisostearate, trimethylolpropane triisostearate, glyceryl triisopalmitate, glyceryl tri 2-ethylhexanoate, glyceryl trimyristate, diparamethoxycinnamic acid-glyceryl monoisooctylate and tri(caprylic acid-capric acid) glycerin.

Examples of the silicone oil include higher alkoxy-modified silicones, alkyl-modified silicones, higher fatty acid ester-modified silicones, such as dimethylpolysiloxane, methylphenylpolysiloxane, methylhydrogenpolysiloxane, octamethylcyclopentasiloxane, decamethyltetrasiloxane, dodecamethylcyclohexasiloxane and stearoxy silicone.

Examples of fat-soluble vitamins include various fat-soluble vitamins and derivatives thereof, for example, tocopherol and derivatives thereof, retinol and derivatives thereof, and ascorbic acid derivatives.

Examples of the saturated linear alcohol include cetanol, stearyl alcohol, cetostearyl alcohol and behenyl alcohol, and examples of the linear monoalkyl glyceryl ether include monocetyl glyceryl ether (chimyl alcohol), monostearyl glyceryl ether (batyl alcohol) and monobehenyl glyceryl ether.

The component C will now be described.

The component C used in the present invention is not specifically limited as far as it is water which can be used in a cosmetic composition, and purified water is preferably used. Water in an aqueous thickener solution or an aqueous solution for adjusting the pH, or water derived from a component added in an oil-in-water emulsion cosmetic composition is also included in the component C used in the present invention.

The component D will now be described.

The component D used in the present invention is a polyhydric alcohol fatty acid ester (excluding the component A) having a hydroxyl value of 100 to 500 and/or a polyhydric alcohol alkyl ether having a hydroxyl value of 100 to 500. When using this component D, it is preferred to use a polyglycerin fatty acid ester having a hydroxyl value of 550 to 700 as the component A.

Furthermore, the component D is more preferably at least one of a polyhydric alcohol fatty acid ester (excluding the component A) having a hydroxyl value of 150 to 500 and a polyhydric alcohol alkyl ether having a hydroxyl value of 150 to 500, and most preferably at least one of a polyhydric alcohol fatty acid ester (excluding the component A) having a hydroxyl value of 200 to 500 and a polyhydric alcohol alkyl ether having a hydroxyl value of 200 to 500.

By using a polyhydric alcohol fatty acid ester (excluding the component A) and a polyhydric alcohol alkyl ether, which have a hydroxyl value within a range from 100 to 500, in combination with a polyglycerin fatty acid ester having a hydroxyl value within a range from 550 to 700 as the component A, the resulting oil-in-water emulsion cosmetic composition has more improved emulsion stability of further improved and more excellent stability against temperature.

As the above-described polyhydric alcohol fatty acid ester (excluding component A) having a hydroxyl value of 100 to 500 and a polyhydric alcohol alkyl ether having a hydroxyl value of 100 to 500, commercially available products can be employed. Examples thereof include glycerin fatty acid ester, sorbitan fatty acid ester, diglycerin fatty acid ester (excluding the component A), polyglycerin fatty acid ester (excluding the component A) having an average polymerization degree of 3 to 10, sucrose fatty acid ester, alkyl glucoside and alkyl glyceryl ether. Among these polyhydric alcohol fatty acid esters, glycerin fatty acid ester, diglycerin fatty acid ester (excluding component A), polyglycerin fatty acid ester (excluding the component A) having an average polymerization degree of 3 to 10 are preferable and diglyceryl monooleate (excluding the component A) is the most preferable. Examples of the commercially available diglyceryl monooleate include products (SUNSOFT® Q-17D) manufactured by Taiyo Kagaku Co., Ltd.

The amounts of the component A, the component B, component C and the component D in the oil-in-water emulsion cosmetic composition of the present invention will now be described.

The amount of the component A in the oil-in-water emulsion cosmetic composition of the present invention is from 0.001 to 25% by mass, preferably from 0.01 to 15% by mass, and particularly preferably from 1 to 10% by mass. When the amount of the component A is less than 0.001%, since the component A can not fulfill the function as the surfactant, an oil-in-water emulsion cosmetic composition can not be obtained. On the other hand, when the amount is more than 25% by mass, characteristics of a functional group of the surfactant itself of the oil-in-water emulsion cosmetic composition strongly appear and the resulting composition exhibits strong greasy feel, and therefore it is undesirable.

The amount of the component B in the oil-in-water emulsion cosmetic composition of the present invention is from 0.001 to 60% by mass, preferably from 0.01 to 50% by mass, and particularly preferably from 1 to 30% by mass. When the amount of the component B is less than 0.001% by mass, characteristics and effects of a functional group peculiar to the oily component of the resulting oil-in-water emulsion cosmetic composition are not obtained. When the amount is more than 60% by mass, not only emulsion stability of the resulting oil-in-water emulsion cosmetic composition becomes inferior, but also greasy feel of the oily component becomes strong.

When using hydrocarbon oil as a portion or all of the component B, the amount of the hydrocarbon oil is preferably from 10 to 100% by mass, more preferably from 15 to 100% by mass, and most preferably from 35 to 100% by mass, based on 100% by mass of the component B. When the amount is within the above range, the particle size of emulsified particles can be more decreased.

The amount of the component C in the oil-in-water emulsion cosmetic composition of the present invention is from 10 to 99% by mass, preferably from 30 to 95% by mass, and particularly preferably from 50 to 90% by mass. When the amount of the component C is less than 10% by mass, emulsion stability becomes inferior. On the other hand, when the amount is more than 99% by mass, the function as the oily component is not exerted and the resulting product is of no value.

When the component D is added to the oil-in-water emulsion cosmetic composition, the amount of the component D is preferably from 1 to 100% by mass, more preferably from 5 to 90% by mass, and most preferably from 10 to 80% by mass, based on the amount of the component A as a polyglycerin fatty acid ester having a hydroxyl value of 550 to 700.

The oil-in-water emulsion cosmetic composition of the present invention may further contain a thickener so as to maintain emulsion stability at high temperature such as 50° C. for a long period.

Examples of the thickener include xanthan gum, guar gum, sodium chondroitin sulfate, sodium hyaluronate, acasia, sodium alginate, carrageenan, methyl cellulose, hydroxypropylmethyl cellulose, hydroxyethyl cellulose, carboxymethyl cellulose, carboxyvinyl polymer, alkyl-added carboxyvinyl polymer, polyvinylalcohol, polyvinyl pyrrolidone and sodium polyacrylate, and these thickeners may be used alone or in combination. The amount of the thickener is preferably from 0.1 to 0.8% by mass, more preferably from 0.1 to 0.7% by mass, and most preferably from 0.1 to 0.6% by mass, based on 100% by mass of the oil-in-water emulsion cosmetic composition.

When using an acidic substance such as carboxyvinyl polymer, an oil-in-water emulsion cosmetic composition can be thickened by preparing an oil-in-water emulsion cosmetic composition, adding an alkali solution (for example, 1% by mass of sodium hydroxide) and adding 1 to 2% by mass of carboxyvinyl polymer aqueous solution. In some cases, an alkali solution may be added after adding a carboxyvinyl polymer aqueous solution.

The oil-in-water emulsion cosmetic composition of the present invention can contain known components used commonly in a cosmetic composition, for example, humectants, powder components, ultraviolet absorbers, antioxidants, beautifying components, lecithin, glycolipids, plant extracts, antiseptics, perfumes, pH adjustors and pigments as far as characteristics of the present invention are not adversely affected.

Examples of the humectant include glycols such as propylene glycol, isoprene glycol, 1,2-pentanediol, 1,3-butylene glycol, dipropylene glycol, hexanediol, polyethylene glycol glycerin, glycerin, diglycerin, triglycerin, polyglycerin, neopentyl glycol, sorbitol, erythritol, pentaerythritol, glucose and galactose; fructose, sucrose, maltose, xylose, xylobiose, reduced oligosaccharide, protein, mucopolysaccharide, collagen, elastin, keratin and triethanolamine.

Examples of the powder component include white inorganic pigments such as titanium oxide, silicone-treated titanium oxide, zinc oxide and barium sulfate; colored inorganic pigments such as iron oxide, carbon black, titanium sintered titanium oxide and ultramarine blue; white extender powders such as talc, silicone-treated talc, white mica, kaolin, silicon carbide, bentonite, smectite, silicic anhydride, aluminum oxide, magnesium oxide, zirconium oxide, diatomaceous earth, calcium silicate, barium silicate, magnesium silicate, calcium carbonate, magnesium carbonate, hydroxyapatite and boron nitride; organic polymer resin powders such as titanium dioxide-coated mica, iron oxide micaceous titanium, silicone-treated micaceous titanium, argentine, polyethylene-based resin, fluorine-based resin, cellulose-based resin and silicone resin; organic low molecular powders such as zinc stearate and N-acryl-lysine; natural organic powders such as starch, silk powder and cellulose powder; organic powder pigments such as Red No. 201, Red No. 202, Orange No. 203, Orange No. 204, Blue Mo. 404 and Yellow No. 401; organic powder pigments made of zirconium, barium or aluminum rake, such as Red No. 3, Red No. 104, Red No. 106, Orange No. 205, Yellow No. 4, Yellow No. 5, Green No. 3 and Blue No. 1; metal powders such as mica and gold powder; and composite powders such as fine titanium oxide particles-coated micaceous titanium.

Examples of the ultraviolet absorber include benzophenone derivative, paraminobenzoic acid derivative, methoxycinnamic acid derivative and urocanic acid.

Examples of the antioxidant include BHT, BHA, vitamin C and derivatives and salts thereof, and vitamin E and derivatives and salts thereof.

Examples of the beautifying component include vitamins including the above vitamins and derivative and salts thereof, anti-inflammatories and herbal medicine.

Examples of the lecithin include soy bean phospholipids and hydrogenated soy bean phospholipids, and examples of glycolipids include sphingoglycolipid.

Examples of plant extract include aloe vera, witch hazel, hamamelis, cucumber, lemon, lavender and rose extracts.

Examples of the antiseptic include methyl paraoxybenzoate, ethyl paraoxybenzoate, butyl paraoxybenzoate, propyl paraoxybenzoate, phenoxyethanol and ethanol.

Examples of the perfume include camphor oil, orange oil, peppermint oil, jasmine absolute, pine oil, lime oil, lavender oil, rose oil and musk tincture.

Examples of the pH adjustor include edetic acid, disodium diedetate, sodium chloride, citric acid, sodium citrate, sodium hydroxide, potassium hydroxide and triethanolamine.

Examples of the pigment include Blue No. 1, Blue No. 204, Red No. 3 and Yellow No. 201.

The oil-in-water emulsion cosmetic composition of the present invention may contain a polyhydric alcohol fatty acid ester having a polyoxyethylene group and a polyhydric alcohol alkyl ether having a polyoxyethylene group, if necessary.

As far as the oil-in-water emulsion cosmetic composition of the present invention is an oil-in-water emulsion cosmetic composition, the kind of a cosmetic composition is not specifically limited. Examples of the oil-in-water emulsion cosmetic composition include cosmetic compositions such as cream in general, milky lotion, sun tan cream, sun-block cream, shaving cream, cleansing cream, facial cleansing cream, lotion in general, sun tan lotion, sun-block lotion, shaving lotion, serum, lipstick, gel and cleansing gel; skincare cosmetic compositions such as moisture gel and pack; makeup cosmetics such as emulsion foundation, emulsified eye shadow and nail treatment; and haircare products such as shampoo, conditioner and hair treatment, and microemulsion having a particle size of 100 nm or less are also included.

As the emulsifying apparatus used in the production of the oil-in-water emulsion cosmetic composition of the present invention, for example, there may be used emulsifying apparatus, which are commonly used in emulsification, such as blade type stirrer, homomixer, disper stirrer and high-pressure homogenizer.

As the emulsification method, for example, there can be used known emulsification methods such as phase inversion temperature emulsification method, phase inversion emulsification method, liquid crystal emulsification method and D phase emulsification method, in addition to self-emulsification method and dispersion emulsification method. More simply, a self-emulsification method is preferably used because an emulsion cosmetic composition having a small emulsified particle size and high storage stability can be obtained. However, the present invention is an invention which is excellent in commodity because an oil-in-water emulsion cosmetic composition having high emulsion stability can be produced even when using an emulsification method.

The method for producing an oil-in-water emulsion cosmetic composition of the present invention will now be described, but is not limited to the following method.

First, an oil phase containing the component A and the component B is charged in a vessel, followed by uniform mixing and further uniform mixing using a disper stirrer to obtain a mixture. The resulting mixture is added to an aqueous phase containing the component C and is self-emulsified by stirring using a disper stirrer (100 to 500 rpm) and thus an oil-in-water emulsion cosmetic composition can be produced. When the component D is added, the oil-in-water emulsion cosmetic composition can be produced by adding the component D to the oil phase.

In this method, since both the components A and B form a lamellar liquid crystal to an aqueous phase thereby to rapidly cause phase inversion, the particle size of the emulsified particles can be decreased similar to the phase inversion emulsification method. Therefore, it is considered that emulsion stability of the resulting oil-in-water emulsion cosmetic composition is improved.

The emulsification temperature is preferably from 10 to 90° C., more preferably from 15 to 85° C., and most preferably from 20 to 80° C.

Although a stirrer is commonly used in this method, an oil-in-water emulsion cosmetic composition can be easily produced by weak stirring due to rotation by hands.

The thickener is preferably added after preparing an oil-in-water emulsion cosmetic composition. Humectants, powder components, ultraviolet absorbers, antioxidants, beautifying components, lecithin, glycolipids, plant extracts, antiseptics, perfumes, pH adjustors and pigments can be added after dissolving in the oil phase containing a component A and a component B if they are dissolved in the oil phase, and those which are dissolved in an aqueous phase containing a component C may be added after dissolving in an aqueous phase, and may be added to an emulsion cosmetic composition after emulsification.

EXAMPLES

Example 1

The present invention will now be described in detail by way of examples, but the present invention is not limited thereto.

[Component Analysis of Polyglycerin as Material]

The compositions of three kinds of polyglycerins (manufactured by Taiyo Kagaku Co., Ltd. under the trade name of Great Oil D-10, Great Oil D-11 and Great Oil D-12) used as the material of a component A of the present invention as well as four kinds of polyglycerins (manufactured by Taiyo Kagaku Co., Ltd. under the trade name of Great Oil S-10, Great Oil S-11, Great Oil S-12 and Great Oil S-13) used as the material of a comparative polyglycerin fatty acid ester were measured by gas chromatography. The analytical results are shown in Table 1. The analytical value of each composition was calculated by a peak area percentage method. In case the polyglycerin contains a dimer or a trimer of a cyclic compound, the analytical values of the compositions of the dimer and the trimer of the polyglycerin indicate values obtained by combining a value of a noncyclic compound and that of a cyclic compound.

TABLE 1

| Polymerization degree | Monomer | Dimer | Trimer | Tetramer | Pentamer | Hexamer | Heptamer | Octamer |
|---|---|---|---|---|---|---|---|---|
| Analysis Example 1 | 6.6 | 6.9 | 7.6 | 8.8 | 9.3 | 9.1 | 8.4 | 7.7 |
| Analysis Example 2 | 0 | 0.7 | 12.5 | 14.1 | 13.6 | 12.3 | 10.5 | 9.4 |
| Analysis Example 3 | 6.0 | 8.9 | 9.5 | 9.5 | 9.6 | 9.0 | 8.1 | 7.3 |
| Analysis Comparative Example 1 | 2.7 | 19.6 | 18.8 | 13.3 | 10.9 | 8.4 | 6.5 | 5.2 |
| Analysis Comparative Example 2 | 0 | 5.7 | 24.2 | 21.5 | 14.9 | 9.9 | 6.9 | 4.8 |
| Analysis Comparative Example 3 | 5.3 | 11.1 | 11.3 | 10.3 | 9.8 | 8.9 | 7.8 | 6.9 |
| Analysis Comparative Example 4 | 0 | 2.1 | 3.7 | 1.8 | 48.3 | 14.8 | 2.2 | 10.8 |

| Polymerization degree | Nonamer | Decamer | Undecamer or Multimer | Total | Dimer cyclic polyglycerin | % Trimer cyclic polyglycerin |
|---|---|---|---|---|---|---|
| Analysis Example 1 | 7.0 | 6.5 | 22.1 | 100.0 | 0.1 | 0.0 |
| Analysis Example 2 | 7.0 | 7.5 | 12.4 | 100.0 | 0 | 0.3 |
| Analysis Example 3 | 6.5 | 6.0 | 19.6 | 100.0 | 1.3 | 1.3 |
| Analysis Comparative Example 1 | 4.1 | 3.6 | 6.9 | 100.0 | 7.8 | 7.9 |
| Analysis Comparative Example 2 | 3.5 | 2.8 | 5.8 | 100.0 | 0 | 0.9 |
| Analysis Comparative Example 3 | 6.0 | 5.5 | 17.1 | 100.0 | 2.6 | 2.6 |
| Analysis Comparative Example 4 | 4.5 | 1.5 | 10.3 | 100.0 | 0 | 1.4 |

*: The above analytical values were calculated by a peak area percentage method.

Polyglycerins of Analysis Examples 1 to 3 and Analysis Comparative Examples 1 to 4 in Table 1 are polyglycerins manufactured by Taiyo Kagaku Co., Ltd. shown in Table 2.

TABLE 2

| | Analyzed polyglycerin (trade name) |
|---|---|
| Analysis Example 1 | Great Oil D-10 |
| Analysis Example 2 | Great Oil D-11 |
| Analysis Example 3 | Great Oil D-12 |
| Analysis Comparative Example 1 | Great Oil S-10 |
| Analysis Comparative Example 2 | Great Oil S-11 |
| Analysis Comparative Example 3 | Great Oil S-12 |
| Analysis Comparative Example 4 | Great Oil S-13 |

[Production of Polyglycerin Fatty Acid Ester]

Using seven kinds of polyglycerins shown in Table 1 as the material, various polyglycerin fatty acid esters each having a different hydroxyl value were synthesized. A method for producing a polyglycerin fatty acid ester using Great Oil D-10 (polyglycerin as the material of Analysis Example 1) as material is shown below.

A 500 ml four-necked flask equipped with a stirrer, a thermometer, a gas blow tube and a water separator, 220 g of a polyglycerin (manufactured by Taiyo Kagaku Co., Ltd. under the trade name of Great Oil D-10), 80 g of isostearic acid and 0.1 g of and tripotassium phosphate were charged and then esterified by heating to a temperature of 200 to 250° C. while stirring in a nitrogen gas flow. After the completion of the reaction, 0.3 ml of phosphoric acid was added to obtain 243 g of a polyglycerin isostearic acid ester used in Example 1. The resulting polyglycerin fatty acid ester had a hydroxyl value of 462.

The following polyglycerin fatty acid esters used in Examples 1 to 14 and Comparative Examples 1 to 15 were produced in the same manner as in case of the method for producing the polyglycerin fatty acid ester used in Example 1, except that a kind of the polyglycerin and the fatty acid in Table 1 were charged in the ratio considering the hydroxyl value of the resulting polyglycerin fatty acid ester. Among constituent fatty acids of the polyglycerin fatty acid esters used in Examples 1 to 14 and Comparative Examples 1 to 15, the content of the fatty acid having 16 to 18 carbon atoms is shown in Table 3 and Table 4.

TABLE 3

Polyglycerin fatty acid ester used in Examples

| Name of material | Hydroxyl value | Polyglycerin used as material | Percentage of fatty acid residue having 16 to 18 carbon atoms based on all constituent fatty acid residues (% by mass) |
|---|---|---|---|
| Polyglycerin isostearic acid ester | 462 | Great Oil D-10 (Analysis Example 1) | 90 |
| Polyglycerin stearic acid ester | 540 | Great Oil D-10 (Analysis Example 1) | 84 |
| Polyglycerin oleic acid ester | 608 | Great Oil D-10 (Analysis Example 1) | 90 |
| Polyglycerin oleic acid ester | 586 | Great Oil D-11 (Analysis Example 2) | 90 |
| Polyglycerin oleic acid ester | 592 | Great Oil D-12 (Analysis Example 3) | 90 |
| Polyglycerin oleic acid ester | 485 | Great Oil D-10 (Analysis Example 1) | 90 |
| Polyglycerin isopalmitic acid ester | 622 | Great Oil D-10 (Analysis Example 1) | 89 |
| Polyglycerin isostearic acid ester | 631 | Great Oil D-10 (Analysis Example 1) | 90 |
| Polyglycerin stearic acid ester | 610 | Great Oil D-10 (Analysis Example 1) | 84 |

TABLE 4

Polyglycerin fatty acid used in Comparative Examples

| Name of material | Hydroxyl value | Polyglycerin used as material | Percentage of fatty acid residue having 16 to 18 carbon atoms based on all constituent fatty acid residues (% by mass) |
|---|---|---|---|
| Polyglycerin oleic acid ester | 480 | Great Oil S-10 (Analysis Comparative Example 1) | 90 |
| Polyglycerin oleic acid ester | 598 | Great Oil S-11 (Analysis Comparative Example 2) | 90 |
| Polyglycerin oleic acid ester | 633 | Great Oil S-12 (Analysis Comparative Example 3) | 90 |

TABLE 4-continued

Polyglycerin fatty acid used in Comparative Examples

| Name of material | Hydroxyl value | Polyglycerin used as material | Percentage of fatty acid residue having 16 to 18 carbon atoms based on all constituent fatty acid residues (% by mass) |
|---|---|---|---|
| Polyglycerin isopalmitic acid ester | 628 | Great Oil S-13 (Analysis Comparative Example 4) | 89 |
| Polyglycerin isostearic acid ester | 423 | Great Oil D-10 (Analysis Example 1) | 90 |
| Polyglycerin stearic acid ester | 710 | Great Oil D-10 (Analysis Example 1) | 84 |
| Polyglycerin myristic acid ester | 604 | Great Oil D-10 (Analysis Example 1) | 45 |
| Polyglycerin behenic acid ester | 611 | Great Oil D-10 (Analysis Example 1) | 36 |
| Polyglycerin oleic acid ester | 462 | Great Oil D-10 (Analysis Example 1) | 90 |
| Polyglycerin oleic acid ester | 485 | Great Oil D-10 (Analysis Example 1) | 90 |

Examples 1 to 14

Oil-in-Water Emulsion Cosmetic Composition

Oil-in-water emulsion cosmetic compositions containing the component A (polyglycerin fatty acid ester obtained from any of polyglycerins of Analysis Examples 1 to 3 as the material), and the components B and C were produced. In Examples other than Examples 1, 2, 6, 9 and 10, the component D was added. The formulations of the resulting oil-in-water emulsion cosmetic compositions are shown in Tables 5 to 10. In Table 5 to Table TO, polyglycerin as the material: Analysis Examples T, 2 and 3 means that the polyglycerins used as the material of the polyglycerin fatty acid ester are polyglycerins as the material of Analysis Examples 1, 2 and 3.

TABLE 5

| | | Formulation (g) | | | | |
|---|---|---|---|---|---|---|
| | Material | Example 1 | Example 2 | Example 3 | Example 4 | Example 5 |
| Component A | Polyglycerin isostearic acid ester Hydroxyl value: 462 Polyglycerin as material: Analysis Example 1 | 2.0 | | | | |
| | Polyglycerin stearic acid ester Hydroxyl value: 540 Polyglycerin as material: Analysis Example 1 | | 2.0 | | | |
| | Polyglycerin oleic acid ester Hydroxyl value: 608 Polyglycerin as material: Analysis Example 1 | | | 1.6 | | |
| | Polyglycerin oleic acid ester Hydroxyl value: 586 Polyglycerin as material: Analysis Example 2 | | | | 1.6 | |
| | Polyglycerin oleic acid ester Hydroxyl value: 592 Polyglycerin as material: Analysis Example 3 | | | | | 1.6 |
| | Polyglycerin oleic acid ester Hydroxyl value: 485 Polyglycerin as material: Analysis Example 1 | | | | | |
| | polyglycerin isopalmitic acid ester Hydroxyl value: 622 Polyglycerin as material: Analysis Example 1 | | | | | |
| | Polyglycerin isostearic acid ester Hydroxyl value: 631 Polyglycerin as material: Analysis Example 1 | | | | | |
| | Polyglycerin stearic acid ester Hydroxyl value: 610 Polyglycerin as material: Analysis Example 1 | | | | | |

TABLE 6

| | | Formulation (g) | | | | |
|---|---|---|---|---|---|---|
| | Material | Example 1 | Example 2 | Example 3 | Example 4 | Example 5 |
| Component B | Liquid paraffin | 20 | 10 | 20 | 20 | 20 |
| | Glyceryl tri 2-ethylhexanoate | | 10 | | | |
| Component D | Diglycerin oleic acid ester Hydroxyl value: 410 | | | 0.4 | 0.4 | 0.4 |
| | Polyglycerin distearic acid ester Hydroxyl value: 430 | | | | | |
| | 1,3-butylene glycol | 10 | | 10 | 10 | 10 |
| Component C | Purified water | 56 | 78 | 56 | 56 | 56 |

TABLE 6-continued

|  | Material | Formulation (g) | | | | |
|---|---|---|---|---|---|---|
|  |  | Example 1 | Example 2 | Example 3 | Example 4 | Example 5 |
| Thickener (containing component C) | 1% by mass carboxyvinyl polymer aqueous solution | 10 |  | 10 | 10 | 10 |
| (containing component C) | 1% by mass sodium hydroxide aquesou solution | 2 |  | 2 | 2 | 2 |
|  | Total | 100 | 100 | 100 | 100 | 100 |

TABLE 7

|  | Material | Formulation (g) | | | | |
|---|---|---|---|---|---|---|
|  |  | Example 6 | Example 7 | Example 8 | Example 9 | Example 10 |
| Component A | Polyglycerin isostearic acid ester Hydroxyl value: 462 Polyglycerin as material: Analysis Example 1 |  |  |  |  | 8.0 |
|  | Polyglycerin stearic acid ester Hydroxyl value: 540 Polyglycerin as material: Analysis Example 1 |  |  |  | 4.0 |  |
|  | Polyglycerin oleic acid ester Hydroxyl value: 608 Polyglycerin as material: Analysis Example 1 |  |  |  |  |  |
|  | Polyglycerin oleic acid ester Hydroxyl value: 586 Polyglycerin as material: Analysis Example 2 |  |  |  |  |  |
|  | Polyglycerin oleic acid ester Hydroxyl value: 592 Polyglycerin as material: Analysis Example 3 |  |  |  |  |  |
|  | Polyglycerin oleic acid ester Hydroxyl value: 485 Polyglycerin as material: Analysis Example 1 | 2.0 |  |  |  |  |
|  | Polyglycerin isopalmitic acid ester Hydroxyl value: 622 Polyglycerin as material: Analysis Example 1 |  | 1.3 |  |  |  |
|  | Polyglycerin isostearic acid ester Hydroxyl value: 631 Polyglycerin as material: Analysis Example 1 |  |  | 1.8 |  |  |
|  | Polyglycerin stearic acid ester Hydroxyl value: 610 Polyglycerin as material: Analysis Example 1 |  |  |  |  |  |

TABLE 8

|  | Material | Formulation (g) | | | | |
|---|---|---|---|---|---|---|
|  |  | Example 6 | Example 7 | Example 8 | Example 9 | Example 10 |
| Component B | Liquid paraffin | 20 | 20 | 20 | 40 | 30 |
|  | Glyceryl tri 2-ethylhexanoate |  |  |  |  |  |
| Component D | Diglycerin oleic acid ester Hydroxyl value: 410 |  | 0.7 | 0.2 |  |  |
|  | Polyglycerin distearic acid ester Hydroxyl value: 430 |  |  |  |  |  |
|  | 1,3-butylene glycol | 10 | 10 | 10 |  |  |
| Component C | Purified water | 56 | 56 | 56 | 56 | 62 |
| Thickener (containing component C) | 1% by mass carboxyvinyl polymer aqueous solution | 10 | 10 | 10 |  |  |
| (containing component C) | 1% by mass sodium hydroxide aquesou solution | 2 | 2 | 2 |  |  |
|  | Total | 100 | 100 | 100 | 100 | 100 |

TABLE 9

|  | Material | Formulation (g) | | | |
|---|---|---|---|---|---|
|  |  | Example 11 | Example 12 | Example 13 | Example 14 |
| Component A | Polyglycerin isostearic acid ester Hydroxyl value: 462 Polyglycerin as material: Analysis Example 1 |  |  |  |  |
|  | Polyglycerin stearic acid ester Hydroxyl value: 540 Polyglycerin as material: Analysis Example 1 |  |  |  |  |
|  | Polyglycerin oleic acid ester Hydroxyl value: 608 Polyglycerin as material: Analysis Example 1 | 1.4 | 1.6 | 3.2 |  |
|  | Polyglycerin oleic acid ester Hydroxyl value: 586 Polyglycerin as material: Analysis Example 2 |  |  |  |  |
|  | Polyglycerin oleic acid ester Hydroxyl value: 592 Polyglycerin as material: Analysis Example 3 |  |  |  |  |

TABLE 9-continued

| | Formulation (g) | | | |
|---|---|---|---|---|
| Material | Example 11 | Example 12 | Example 13 | Example 14 |
| Polyglycerin oleic acid ester Hydroxyl value: 485 Polyglycerin as material: Analysis Example 1 | | | | |
| Polyglycerin isopalmitic acid ester Hydroxyl value: 622 Polyglycerin as material: Analysis Example 1 | | | | |
| Polyglycerin isostearic acid ester Hydroxyl value: 631 Polyglycerin as material: Analysis Example 1 | | | | |
| Polyglycerin stearic acid ester Hydroxyl value: 610 Polyglycerin as material: Analysis Example 1 | | | | 1.6 |

TABLE 10

| | | Formulation (g) | | | |
|---|---|---|---|---|---|
| | Material | Example 11 | Example 12 | Example 13 | Example 14 |
| Component B | Liquid paraffin | 10 | 20 | 18 | 20 |
| | Glyceryl tri 2-ethylhexanoate | 10 | | 18 | |
| Component D | Diglycerin oleic acid ester Hydroxyl value: 410 | | 0.4 | 0.8 | 0.4 |
| | Polyglycerin distearic acid ester Hydroxyl value: 430 | 0.6 | | | |
| | 1,3-butylene glycol | 10 | 10 | | 10 |
| Component C | Purified water | 56 | 56 | 60 | 56 |
| Thickener (containing component C) | 1% by mass carboxyvinyl polymer aqueous solution | 10 | 10 | | 10 |
| (containing component C) | 1% by mass sodium hydroxide aqueous solution | 2 | 2 | 2 | |
| | Total | 100 | 100 | 100 | 100 |

[Production of Oil-in-Water Emulsion Cosmetic Composition of Example 1 (Self-Emulsification Method)]

According to the formulations shown in Tables 5 and 6, oil-in-water emulsion cosmetic compositions were produced in the following manner.

The component A and the component B were charged in a 100 ml stainless steel vessel and then mixed and dissolved by disper stirring (1,000 rpm) at 70° C. to obtain an oil phase. In a 300 ml stainless steel vessel, purified water as the component C and 1,3-butylene glycol were mixed and dissolved by disper stirring (1,000 rpm) at 70° C. to obtain an aqueous phase. The oil phase at 70° C. was added to the aqueous phase while stirring at 70° C. using a disper stirrer (1,000 rpm).

While continuing disper stirring, a 1% by mass sodium hydroxide aqueous solution (containing the component C) was added, followed by the addition of a 1% by mass carboxyvinyl polymer aqueous solution (containing the component C) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 98 g of an oil-in-water emulsion cosmetic composition.

[Production of Oil-in-Water Emulsion Cosmetic Compositions of Examples 2 to 11 and 13 to 14]

According to the formulations shown in Tables 5 to 10, oil-in-water emulsion cosmetic compositions of Examples 2 to 11 and 13 to 14 were produced by the same self-emulsification method as that in case of the oil-in-water emulsion cosmetic composition of Example 1. Among the oil-in-water emulsion cosmetic compositions of Examples 2 to 11 and 13 to 14, oil-in-water emulsion cosmetic compositions containing the component D were produced by charging the components A, B, and D in a 100 ml stainless steel vessel to prepare an oil phase.

[Production of Oil-in-Water Emulsion Cosmetic Composition of Example 12 (Phase Inversion Emulsification Method)]

According to the formulations shown in Tables 9 and 10, an oil-in-water emulsion cosmetic composition was produced by the following method.

Purified water heated to 70° C. as the component C and 1,3-butylene glycol were charged in a 300 ml stainless steel vessel and then mixed and dissolved by disper stirring (1,000 rpm) at 70° C. to obtain an aqueous phase. The components A, B, and D were mixed and dissolved by disper stirring (1,000 rpm) at 70° C. to obtain an oil phase.

The oil phase was stirred (3,000 rpm) in a disper stirrer and the aqueous phase at 70° C. was added therein, followed by disper stirring at 70° C. for 20 minutes.

While continuing disper stirring, a 1% by mass sodium hydroxide aqueous solution (containing the component C) was added, followed by the addition of a 1% by mass carboxyvinyl polymer aqueous solution (containing the component C) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 98 g of an oil-in-water emulsion cosmetic composition.

Comparative Examples 1 to 15

Oil-in-Water Emulsion Cosmetic Composition

Oil-in-water emulsion cosmetic compositions containing a polyglycerin fatty acid ester obtained from any of polyglycerins of Analysis Comparative Examples 1 to 4 as the material, and the components B and C were produced. Oil-in-water emulsion cosmetic compositions of Comparative Examples 2 to 9 also contained a component D. The formulations of the oil-in-water emulsion cosmetic composition thus produced are shown in Table 11 to Table 16. In Tables 11 to 16, polyglycerin as the material: Analysis Comparative Examples 1, 2, 3 and 4 indicates that polyglycerins used as the material of the polyglycerin fatty acid ester are polyglycerins as the material of Analysis Comparative Examples 1, 2, 3 and 4.

TABLE 11

| Material | Comparative Example 1 | Comparative Example 2 | Comparative Example 3 | Comparative Example 4 | Comparative Example 5 |
|---|---|---|---|---|---|
| Polyglycerin oleic acid ester Hydroxyl value: 480 Polyglycerin as material: Analysis Comparative Example 1 | 2.0 | | | | |
| Polyglycerin oleic acid ester Hydroxyl value: 598 Polyglycerin as material: Analysis Comparative Example 2 | | 1.5 | | | |
| Polylycerin oleic acid ester Hydroxyl value: 633 Polyglycerin as material: Analysis Comparative Example 3 | | | 1.6 | | |
| Polyglycerin isopalmitic acid ester Hydroxyl value: 628 Polyglycerin as material: Analysis Comparative Example 4 | | | | 1.3 | |
| Polyglycerin isostearic acid ester Hydroxyl value: 423 Polyglycerin as material: Analysis Example 1 | | | | | 1.8 |
| Polyglycerin stearic acid ester Hydroxyl value: 710 Polyglycerin as material: Analysis Example 1 | | | | | |
| polyglycerin myristic acid ester Hydroxyl value: 604 Polyglycerin as material: Analysis Example 1 | | | | | |
| Polyglycerin behenic acid ester Hydroxyl value: 611 Polyglycerin as material: Analysis Example 1 | | | | | |
| Polyglycerin oleic acid ester Hydroxyl value: 462 Polyglycerin as material: Analysis Example 1 | | | | | |
| Polyglycerin oleic acid ester Hydroxyl value: 485 Polyglycerin as material: Analysis Example 1 | | | | | |

TABLE 12

| | Material | Comparative Example 1 | Comparative Example 2 | Comparative Example 3 | Comparative Example 4 | Comparative Example 5 |
|---|---|---|---|---|---|---|
| Component B | Liquid paraffin | 20 | 10 | 20 | 20 | 20 |
| | Glyceryl tri 2-ethylhexanoate | | 10 | | | |
| Component D | Diglycerin oleic acid ester Hydroxyl value: 410 | | 0.5 | 0.4 | 0.7 | 0.2 |
| | Polyglycerin distearic acid ester Hydroxyl value: 430 | | | | | |
| | 1,3-butylene glycol | 10 | 10 | 10 | 10 | 10 |
| Component C | Purified water | 56 | 56 | 56 | 56 | 56 |
| Thickener (containing component C) | 1% by mass carboxyvinyl polymer aqueous solution | 10 | 10 | 10 | 10 | 10 |
| (containing component C) | 1% by mass sodium hydroxide aquesou solution | 2 | 2 | 2 | 2 | 2 |
| | Total | 100 | 100 | 100 | 100 | 100 |

TABLE 13

| Material | Comparative Example 6 | Comparative Example 7 | Comparative Example 8 | Comparative Example 9 | Comparative Example 10 |
|---|---|---|---|---|---|
| Polyglycerin oleic acid ester Hydroxyl value: 480 Polyglycerin as material: Analysis Comparative Example 1 | | | | | |
| Polyglycerin oleic acid ester Hydroxyl value: 598 Polyglycerin as material: Analysis Comparative Example 2 | | 1.4 | | | |
| Polyglycerin oleic acid ester Hydroxyl value: 633 Polyglycerin as material: Analysis Comparative Example 3 | | | | | |
| Polyglycerin isopalmitic acid ester Hydroxyl value: 628 Polyglycerin as material: Analysis Comparative Example 4 | | | | | |
| Polyglycerin isostearic acid ester Hydroxyl value: 423 Polyglycerin as material: Analysis Example 1 | | | | | |
| Polyglycerin stearic acid ester Hydroxyl value: 710 Polyglycerin as material: Analysis Example 1 | 1.8 | | | | |
| polyglycerin myristic acid ester Hydroxyl value: 604 Polyglycerin as material: Analysis Example 1 | | | 1.2 | | |
| polyglycerin behenic acid ester Hydroxyl value: 611 | | | | 1.9 | |

TABLE 13-continued

|  | Formulation (g) | | | | |
| --- | --- | --- | --- | --- | --- |
| Material | Comparative Example 6 | Comparative Example 7 | Comparative Example 8 | Comparative Example 9 | Comparative Example 10 |
| Polyglycerin as material: Analysis Example 1 | | | | | |
| Polyglycerin oleic acid ester Hydroxyl value: 462 | | | | | |
| Polyglycerin as material: Analysis Example 1 | | | | | |
| Polyglycerin oleic acid ester Hydroxyl value: 485 | | | | | 30 |
| Polyglycerin as material: Analysis Example 1 | | | | | |

TABLE 14

|  |  | Formulation (g) | | | | |
| --- | --- | --- | --- | --- | --- | --- |
|  | Material | Comparative Example 6 | Comparative Example 7 | Comparative Example 8 | Comparative Example 9 | Comparative Example 10 |
| Component B | Liquid paraffin | 20 | 20 | 10 | 20 | 20 |
|  | Glyceryl tri 2-ethylhexanoate |  |  | 10 | 10 | 10 |
| Component D | Diglycerin oleic acid ester Hydroxyl value: 410 | 0.2 |  | 0.8 | 0.1 |  |
|  | Polyglycerin distearic acid ester Hydroxyl value: 430 |  | 0.6 |  |  |  |
|  | 1,3-butylene glycol | 10 | 10 | 10 | 10 |  |
| Component C | Purified water | 56 | 56 | 56 | 46 | 40 |
| Thickener (containing component C) | 1% by mass carboxyvinyl polymer aqueous solution | 10 | 10 | 10 | 10 |  |
| (containing component C) | 1% by mass sodium hydroxide aqusou solution | 2 | 2 | 2 | 2 |  |
|  | Total | 100 | 100 | 100 | 100 | 100 |

TABLE 15

|  | Formulation (g) | | | | |
| --- | --- | --- | --- | --- | --- |
| Material | Comparative Example 11 | Comparative Example 12 | Comparative Example 13 | Comparative Example 14 | Comparative Example 15 |
| Polyglycerin oleic acid ester Hydroxyl value: 480 | | | | | |
| Polyglycerin as material: Analysis Comparative Example 1 | | | | | |
| Polyglycerin oleic acid ester Hydroxyl value: 598 | | | | | |
| Polyglycerin as material: Analysis Comparative Example 2 | | | | | |
| Polyglycerin oleic acid ester Hydroxyl value: 633 | | | | | |
| Polyglycerin as material: Analysis Comparative Example 3 | | | | | |
| Polyglycerin isopalmitic acid ester Hydroxyl value: 628 | | | | | |
| Polyglycerin as material: Analysis Comparative Example 4 | | | | | |
| Polyglycerin isostearic acid ester Hydroxyl value: 423 | | | | | |
| Polyglycerin as material: Analysis Example 1 | | | | | |
| Polyglycerin stearic acid ester Hydroxyl value: 710 | | | | | |
| Polyglycerin as material: Analysis Example 1 | | | | | |
| polyglycerin myristic acid ester Hydroxyl value: 604 | | | | | |
| Polyglycerin as material: Analysis Example 1 | | | | | |
| polyglycerin behenic acid ester Hydroxyl value: 611 | | | | | |
| Polyglycerin as material: Analysis Example 1 | | | | | |
| Polyglycerin oleic acid ester Hydroxyl value: 462 | 5.0 | 20 | 0.0005 | | |
| Polyglycerin as material: Analysis Example 1 | | | | | |
| Polyglycerin oleic acid ester Hydroxyl value: 485 | | | | 0.005 | 0.1 |
| Polyglycerin as material: Analysis Example 2 | | | | | |

TABLE 16

|  |  | Formulation (9) | | | | |
| --- | --- | --- | --- | --- | --- | --- |
|  | Material | Comparative Example 11 | Comparative Example 12 | Comparative Example 13 | Comparative Example 14 | Comparative Example 15 |
| Component B | Liquid paraffin | 65 | 55 | 0.005 | 0.0005 | 0.5 |
|  | Glyceryl tri 2-ethylhexanoate |  |  |  |  |  |
| Component D | Diglycerin oleic acid ester Hydroxyl value: 410 |  |  |  |  |  |
|  | Polyglycerin distearic acid ester |  |  |  |  |  |

TABLE 16-continued

| | | Formulation (9) | | | | |
|---|---|---|---|---|---|---|
| | Material | Comparative Example 11 | Comparative Example 12 | Comparative Example 13 | Comparative Example 14 | Comparative Example 15 |
| Component C<br>Thickener<br>(containing Component C)<br>(containing component C) | Hydroxyl value: 430<br>1,3-butylene glycol<br>Purified water<br>1% by mass carboxyvinyl polymer aqueous solution<br>1% by mass sodium hydroxide aquesou solution | 30 | 20<br>5 | 10<br>77.9945<br>10<br>2 | 10<br>77.9945<br>10<br>2 | 99.4 |
| | Total | 100 | 100 | 100 | 100 | 100 |

[Production of Comparative Oil-in-Water Emulsion Cosmetic Composition of Comparative Example 1 (Self-Emulsification Method)]

According to the formulations shown in Tables 11 and 12, an oil-in-water emulsion cosmetic composition was produced by the following method.

A polyglycerin fatty acid ester obtained from polyglycerin of Analysis Comparative Example 1 as the material and the component B were charged in 100 ml of a stainless steel vessel and then mixed and dissolved by disper stirring (1,000 rpm) at 70° C. to obtain an oil phase. In a 300 ml stainless steel vessel, purified water as the component C and 1,3-butylene glycol were mixed and dissolved by disper stirring (1,000 rpm) at 70° C. to obtain an aqueous phase.

Then, the oil phase at 70° C. was added to the aqueous phase while stirring by a disper stirrer (1,000 rpm) at 70° C.

While continuing disper stirring, a 1% by mass sodium hydroxide aqueous solution (containing the component C) was added, followed by the addition of a 1% by mass carboxyvinyl polymer aqueous solution (containing the component C) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 98 g of an oil-in-water emulsion cosmetic composition.

[Production of Oil-in-Water Emulsion Cosmetic Compositions of Comparative Examples 2 to 15 (Self-Emulsification Method)]

According to the formulations shown in Tables 11 to 16, oil-in-water emulsion cosmetic compositions of Comparative Examples 2 to 12 were produced by the same self-emulsification method as that in case of a comparative oil-in-water emulsion cosmetic composition of Comparative Example 1. Among the oil-in-water emulsion cosmetic compositions of Comparative Examples 2 to 15, oil-in-water emulsion cosmetic compositions containing the component D were produced by charging the components B and D in a 100 ml stainless steel vessel to prepare an oil phase.

With respect to the resulting oil-in-water emulsion cosmetic compositions, stability against temperature, sensory evaluation and physical properties were evaluated. The evaluation will now be described in detail.

[Evaluation of Stability against Temperature]

(1) High Temperature Stability

An oil-in-water emulsion cosmetic composition was stored while standing at 50° C. for one month and it was observed whether or not separation or creaming of an oil phase occurred. Samples where a stable state was maintained were rated "Stable", samples where creaming occurred were rated "Creaming", and samples where oil phase separation occurred were rated "Separated".

When samples are rated stable by this evaluation, they can be recognized as an emulsion cosmetic composition which maintains stable emulsification even in a high temperature state during storage and circulation.

(2) Low Temperature Stability

An oil-in-water emulsion cosmetic composition was stored while standing at 5° C. for 6 months and it was observed whether or not separation or creaming of an oil phase occurred. Samples where a stable state was maintained were rated "Stable", samples where creaming occurred were rated "Creaming", and samples where oil phase separation occurred were rated "Separated".

When samples are rated stable by this evaluation, they can be recognized as an emulsion cosmetic composition which maintains stable emulsification even in a low temperature state during storage and circulation.

(3) Stability Against Temperature Variation

An oil-in-water emulsion cosmetic composition was stored while controlling the temperature to −10° C. and 40° C. every 24 hours for one month and it was observed whether or not separation or creaming of an oil phase occurred. Samples where a stable state was maintained were rated "Stable", samples where creaming occurred were rated "Creaming", and samples where oil phase separation occurred were rated "Separated".

When samples are rated stable by this evaluation, they can be recognized as an emulsion cosmetic composition which maintains stable emulsification against a temperature change during storage and circulation.

(4) Stability against High Temperature Shaking

In a shaking bath manufactured by Yamato Scientific Co., Ltd., a 20 ml glass-stoppered test tube filled with 10 ml of an oil-in-water emulsion cosmetic composition was set. After shaking back and forth between two points separated by a distance of 3 cm at a speed of 60 times/min. and a temperature of 50° C. for 24 hours, it was observed whether or not separation or creaming of an oil phase occurred. Samples where a stable state was maintained were rated "Stable", samples where creaming occurred were rated "Creaming", and samples where oil phase separation occurred were rated "Separated".

When samples are rated stable by this evaluation, they can be recognized as an emulsion cosmetic composition which maintains stable emulsification against impact during circulation.

[Sensory Evaluation]

Twenty panelists conducted sensory evaluation of an oil-in-water emulsion cosmetic composition was conducted by evaluating four items such as texture, greasy feel, transparent feel and compatibility (rapidly compatible with skin). Specifically, twenty panelists were asked to give a score according to sensory evaluation criteria with respect to four items when the oil-in-water emulsion cosmetic composition was applied to the facies medialis brachii, and then an average of scores of twenty panelists was calculated. As the average of scores approaches to 4, the sensory evaluation results become better, and therefore tactile sensation is considered as excellent. To the contrary, as the average of scores approaches to 0, the sensory evaluation results become worse, and therefore tactile sensation is considered as poor. Sensory evaluation was rated by five-rank criteria, that is, A, B, C, D and E.

Sensory evaluation criteria of four evaluation items are shown in Tables 11 to 14. When texture and viscosity of the resulting oil-in-water emulsion cosmetic composition are almost the same as those of ordinary water, the measurement or evaluation was not conducted.

TABLE 17

(1) Sensory evaluation criteria for textile and indication

| Sensory evaluation criteria | | Indication of sensory evaluation | |
|---|---|---|---|
| Scores | Evaluation results | Average of scores | Sensory evaluation |
| 4 | Excellent texture | 3.5-4 | A |
| 3 | Ordinary texture | 3.0-3.4 | B |
| 2 | Slight texture | 2.0-2.9 | C |
| 1 | Nearly no texture | 1.0-1.9 | D |
| 0 | No texture | 0-0.9 | E |

TABLE 18

(2) Sensory evaluation criteria for greasy feel and indication

| Sensory evaluation criteria | | Indication of sensory evaluation | |
|---|---|---|---|
| Scores | Evaluation results | Average of scores | Sensory evaluation |
| 4 | No greasy feel | 3.5-4 | A |
| 3 | Nearly no greasy feel | 3.0-3.4 | B |
| 2 | Slight greasy feel | 2.0-2.9 | C |
| 1 | Some greasy feel | 1.0-1.9 | D |
| 0 | Very greasy feel | 0-0.9 | E |

TABLE 19

(3) Sensory evaluation criteria for transparent feel and indication

| Sensory evaluation criteria | | Indication of sensory evaluation | |
|---|---|---|---|
| Scores | Evaluation results | Average of scores | Sensory evaluation |
| 4 | Excellent transparent feel | 3.5-4 | A |
| 3 | Ordinary transparent feel | 3.0-3.4 | B |
| 2 | Slight transparent feel | 2.0-2.9 | C |
| 1 | Poor transparent feel | 1.0-1.9 | D |
| 0 | No transparent feel | 0-0.9 | E |

TABLE 20

(4) Sensory evaluation criteria for compatibility and indication

| Sensory evaluation criteria | | Indication of sensory evaluation | |
|---|---|---|---|
| Scores | Evaluation results | Average of scores | Sensory evaluation |
| 4 | Excellent compatibility | 3.5-4 | A |
| 3 | Ordinary compatibility | 3.0-3.4 | B |
| 2 | Slightly poor compatibility | 2.0-2.9 | C |
| 1 | Poor compatibility | 1.0-1.9 | D |
| 0 | Very poor compatibility | 0-0.9 | E |

[Evaluation of Physical Properties]
(1) Average Emulsified Particle Size (nm or μm)

The resulting oil-in-water emulsion cosmetic composition was diluted with purified water and an average emulsified particle size was measured using a particle size distribution analyzer LA-300 manufactured by Horiba, Ltd. With respect to those having an average emulsified particle size of 0.1 μm or less, the measurement was conducted using a particle size distribution analyzer N4PLUS manufactured by Beckman Coulter Co.

(2) Viscosity (Unit: mPa·s)

Using a B type viscometer manufactured by Tokyo Keiki Co., Ltd., viscosity of an oil-in-water emulsion cosmetic composition was measured under the conditions of 25° C., rotor No. 3, 6 rpm and 1 min.

(3) pH Value

Using a pH meter manufactured by Horiba, Ltd., pH at 25° C. of oil-in-water emulsion cosmetic composition was measured.

The results of stability against temperature, sensory evaluation and physical properties of the resulting oil-in-water emulsion cosmetic compositions of Examples 1 to 14 and Comparative Examples 1 to 15 are shown in Tables 21 to 26.

TABLE 21

| Evaluation items | Example 1 | Example 2 | Example 3 | Example 4 | Example 5 | Example 6 |
|---|---|---|---|---|---|---|
| High temperature stability | Stable | Stable | Stable | Stable | Stable | Stable |
| Low temperature stability | Stable | Stable | Stable | Stable | Stable | Stable |
| Stability against temperature variation | Stable | Stable | Stable | Stable | Stable | Stable |
| Stability against high temperature shaking | Stable | Stable | Stable | Stable | Stable | Stable |
| Texture | A | A | A | A | A | A |
| Greasy feel | A | A | A | A | A | A |
| Transparent feel | A | A | A | A | A | A |
| Compatibility | A | A | A | A | A | A |
| Average emulsified particle size (μm) | 0.60 | 0.58 | 0.64 | 0.65 | 0.51 | 0.68 |
| Viscosity (mPa · s) | 6100 | 2900 | 6000 | 7500 | 7600 | 8100 |
| pH value | 6.51 | 6.01 | 6.52 | 6.24 | 5.85 | 6.01 |

TABLE 22

| Evaluation items | Example 7 | Example 8 | Example 9 | Example 10 | Example 11 | Example 12 |
| --- | --- | --- | --- | --- | --- | --- |
| High temperature stability | Stable | Stable | Stable | Stable | Stable | Stable |
| Low temperature stability | Stable | Stable | Stable | Stable | Stable | Stable |
| Stability against temperature variation | Stable | Stable | Stable | Stable | Stable | Stable |
| Stability against high temperature shaking | Stable | Stable | Stable | Stable | Stable | Stable |
| Texture | A | A | A | A | A | A |
| Greasy feel | A | A | A | A | A | A |
| Transparent feel | A | A | A | A | A | A |
| Compatibility | B | A | A | A | A | A |
| Average emulsified particle size (μm) | 0.71 | 0.59 | 0.51 | 0.78 | 0.73 | 0.90 |
| Viscosity (mPa·s) | 8300 | 9600 | 2600 | 2900 | 9100 | 7000 |
| pH value | 6.24 | 6.32 | 5.85 | 6.01 | 6.64 | 6.32 |

TABLE 23

| Evaluation items | Example 13 | Example 14 |
| --- | --- | --- |
| High temperature stability | Stable | Stable |
| Low temperature stability | Stable | Stable |
| Stability against temperature variation | Stable | Stable |
| Stability against high temperature shaking | Stable | Stable |
| Texture | A | A |
| Greasy feel | B | A |
| Transparent feel | B | A |
| Compatibility | A | A |
| Average emulsified particle size (μm) | 0.49 | 0.56 |
| Viscosity (mPa·s) | 2000 | 8600 |
| pH value | 6.11 | 6.64 |

TABLE 24

| Evaluation items | Comparative Example 1 | Comparative Example 2 | Comparative Example 3 | Comparative Example 4 | Comparative Example 5 | Comparative Example 6 |
| --- | --- | --- | --- | --- | --- | --- |
| High temperature stability | Separated | Separated | Separated | Separated | Separated | Separated |
| Low temperature stability | Creaming | Creaming | Creaming | Creaming | Creaming | Creaming |
| Stability against temperature variation | Separated | Separated | Separated | Separated | Separated | Separated |
| Stability against high temperature shaking | Separated | Separated | Separated | Separated | Separated | Separated |
| Texture | A | A | A | A | A | A |
| Greasy feel | A | A | A | A | A | A |
| Transparent feel | A | B | A | B | A | B |
| Compatibility | A | A | A | A | A | B |
| Average emulsified particle size (μm) | 1.84 | 1.95 | 1.72 | 1.95 | 1.91 | 2.01 |
| Viscosity (mPa·s) | 8300 | 7600 | 7500 | 8200 | 8600 | 8200 |
| pH value | 6.54 | 6.13 | 5.32 | 6.66 | 5.98 | 6.02 |

TABLE 25

| Evaluation items | Comparative Example 7 | Comparative Example 8 | Comparative Example 9 | Comparative Example 10 | Comparative Example 11 | Comparative Example 12 |
| --- | --- | --- | --- | --- | --- | --- |
| High temperature stability | Creaming | Separated | Separated | Separated | Stable | Separated |
| Low temperature stability | Stable | Separated | Stable | Stable | Stable | Separated |
| Stability against temperature variation | Creaming | Separated | Creaming | Separated | Stable | Separated |
| Stability against high temperature shaking | Separated | Separated | Separated | Separated | Separated | Separated |
| Texture | C | C | E | C | C | C |
| Greasy feel | B | C | C | E | E | C |
| Transparent feel | C | C | E | C | D | D |
| Compatibility | A | A | A | C | C | C |
| Average emulsified particle size (μm) | 1.97 | 1.85 | 1.98 | 1.79 | 1.85 | 2.97 |
| Viscosity (mPa·s) | 8200 | 7400 | 6200 | 4600 | 4300 | 4200 |
| pH value | 6.33 | 6.43 | 6.34 | 6.55 | 6.35 | 6.45 |

TABLE 26

| Evaluation items | Comparative Example 13 | Comparative Example 14 | Comparative Example 15 |
|---|---|---|---|
| High temperature stability | Separated | Separated | Stable |
| Low temperature stability | Separated | Stable | Stable |
| Stability against temperature variation | Separated | Separated | Separated |
| Stability against high temperature shaking | Separated | Separated | Separated |
| Texture | — | — | — |
| Greasy feel | B | B | B |
| Transparent feel | B | B | B |
| Compatibility | B | B | B |
| Average emulsified particle size (μm) | 0.33 | 0.45 | 0.65 |
| Viscosity (mPa · s) | — | — | — |
| pH value | 6.43 | 6.40 | 6.33 |

*: The symbol — means "impossible to evaluate or measure"

As is apparent from the results shown in Tables 21 to 26, the oil-in-water emulsion cosmetic composition of Examples 1 to 14 are excellent in high temperature stability, low temperature stability, stability against temperature variation, stability against high temperature shaking and have texture and transparent feel, and are also free from greasy feel and are excellent in compatibility. To the contrary, the oil-in-water emulsion cosmetic compositions of Comparative Examples 1 to 15 were inferior in emulsion stability as compared with the oil-in-water emulsion cosmetic compositions of Examples 1 to 14.

Example 15

Emollient Cream

According to the formulation shown in Table 27, an emollient cream as an oil-in-water emulsion cosmetic composition was produced.

First, materials (1) to (7) were charged in a 100 ml stainless steel vessel and then mixed and dissolved by disper stirring (3,000 rpm) while heating to 70° C. to obtain an oil phase. Materials (8) to (11) were mixed and dissolved by disper stirring (1,000 rpm) at 70° C. to obtain an aqueous phase. Then, the oil phase at 70° C. was added to the aqueous phase while stirring by a disper stirrer (1,000 rpm) at 70° C.

While continuing disper stirring, a material (12) was added, followed by the addition of a material (13) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 96 g of an emollient cream as an oil-in-water emulsion cosmetic composition.

With respect to the resulting emollient cream, stability against temperature, sensory evaluation and physical properties were evaluated. The evaluation results are shown in Table 28. The evaluation was conducted in the same manner as in case of the above-described evaluation of the oil-in-water emulsion cosmetic compositions of Examples 1 to 14. From the evaluation results, it was confirmed that the emollient cream of Example 15 is an oil-in-water emulsion cosmetic composition which is excellent in stability and is also excellent in tactile sensation.

TABLE 27

Example 15

| | Material No. | Material | Amount (g) |
|---|---|---|---|
| Component A | (1) | Polyglycerin fatty acid ester used in Example 1 | 3.0 |
| Component B | (2) | Neopentyl glycol dicaprate | 12.0 |
| | (3) | Squalane | 16.0 |
| | (4) | Microcrystalline wax | 2.0 |
| | (5) | Dimethylpolysiloxane | 0.1 |
| | (6) | Cetanol | 1.2 |
| | (7) | Stearyl alcohol | 1.2 |
| | (8) | Methyl paraben | 0.1 |
| | (9) | Propylene glycol | 12.0 |
| | (10) | Glycerin | 4.0 |
| Component C | (11) | Purified water | 37.4 |
| | (12) | Triethanolamine | 1.0 |
| Thickener (containing component C) | (13) | 1% carboxyvinyl polymer aqueous solution | 10.0 |
| | | Total | 100.0 |

TABLE 28

| Evaluation items | Example 15 |
|---|---|
| High temperature stability | Stable |
| Low temperature stability | Stable |
| Stability against temperature variation | Stable |
| Stability against high temperature shaking | Stable |
| Texture | A |
| Greasy feel | A |
| Transparent feel | A |
| Compatibility | A |
| Average emulsified particle size (μm) | 0.84 |
| Viscosity (mPa · s) | 22000 |
| pH value | 6.52 |

Example 16

Milky Lotion 1

According to the formulation shown in Table 29, a milky lotion as an oil-in-water emulsion cosmetic composition was produced.

First, materials (1) to (5) were charged in a 100 ml stainless steel vessel and then mixed and dissolved by disper stirring (1,000 rpm) while heating to 70° C. to obtain an oil phase. Materials (6) and (7) were mixed and dissolved by disper stirring (1,000 rpm) at 75° C. to obtain an aqueous phase. Then, the oil phase at 70° C. was added to the aqueous phase while stirring by a disper stirrer (1,000 rpm) at 70° C.

While continuing disper stirring, a material (8) was added, followed by the addition of a material (9) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 97 g of a milky lotion as an oil-in-water emulsion cosmetic composition.

With respect to the resulting milky lotion, stability against temperature, sensory evaluation and physical properties were evaluated. The evaluation results are shown in Table 30. The evaluation was conducted in the same manner as in case of the above-described evaluation of the oil-in-water emulsion cosmetic compositions of Examples 1 to 14.

From the evaluation results, it was confirmed that the emollient cream of Example 16 is an oil-in-water emulsion cosmetic composition which is excellent in stability and is also excellent in tactile sensation.

TABLE 29

Example 16

| | Material No. | Material | Amount (g) |
|---|---|---|---|
| Component A | (1) | Polyglycerin fatty acid ester used in Example 2 | 0.5 |
| Component B | (2) | Neopentyl glycol dicaprare | 1.0 |
| | (3) | Liquid paraffin | 2.0 |
| | (4) | Macadamia nuts oil | 1.5 |
| | (5) | Cetostearyl alcohol | 0.5 |
| | (6) | 1,3-butylene glycol | 18.0 |
| Component C | (7) | Purified water | 56.5 |
| Thickener (containing component C) | (8) | 2% xanthan gum aqueous solution | 10 |
| | (9) | 2% hydroxypropylmethyl cellulose aqueous solution | 10 |
| | | Total | 100.0 |

TABLE 30

| Evaluation items | Example 16 |
|---|---|
| High temperature stability | Stable |
| Low temperature stability | Stable |
| Stability against temperature variation | Stable |
| Stability against high temperature shaking | Stable |
| Texture | A |
| Greasy feel | A |
| Transparent feel | A |
| Compatibility | A |
| Average emulsified particle size (μm) | 0.48 |
| Viscosity (mPa · s) | 10100 |
| pH value | 5.56 |

Example 17

Milky Lotion 2

According to the formulation shown in Table 31, a milky lotion as an oil-in-water emulsion cosmetic composition was produced.

First, materials (1) to (4) were charged in a 50 ml stainless steel vessel and then mixed and dissolved by disper stirring (1,000 rpm) while heating to 70° C. to obtain an oil phase. Materials (5) to (7) were mixed and dissolved by disper stirring (1,000 rpm) at 75° C. to obtain an aqueous phase. Then, the oil phase at 70° C. was added to the aqueous phase while stirring by a disper stirrer (1,000 rpm) at 70° C.

While continuing disper stirring, a material (8) was added, followed by the addition of a material (9) and further disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 97 g of a milky lotion as an oil-in-water emulsion cosmetic composition.

With respect to the resulting milky lotion, stability against temperature, sensory evaluation and physical properties were evaluated. The evaluation results are shown in Table 32. The evaluation was conducted in the same manner as in case of the above-described evaluation of the oil-in-water emulsion cosmetic compositions of Examples 1 to 14.

From the evaluation results, it was confirmed that the emollient cream of Example 17 is an oil-in-water emulsion cosmetic composition which is excellent in stability and is also excellent in tactile sensation.

TABLE 31

Example 17

| | Material No. | Material | Amount (g) |
|---|---|---|---|
| Component A | (1) | Polyglycerin fatty acid ester used in Example 3 | 0.4 |
| Component B | (2) | Liquid paraffin | 2.0 |
| | (3) | Glyceryl tri 2-ethylhexanoate | 3.0 |
| Component D | (4) | Diglycerin oleic acid ester (Hydroxyl value: 410) | 0.1 |
| | (5) | Glycerin | 5.0 |
| | (6) | 1.3-butylene glycol | 10.0 |
| Component C (containing component C) | (7) | Purified water | 67.5 |
| | (8) | 1% sodium hydroxide aquesou solution | 2.0 |
| Thickener (containing component C) | (9) | 1% carboxyvinyl polymer aquesou solution | 10.0 |
| | | Total | 100.0 |

TABLE 32

| Evaluation items | Example 17 |
|---|---|
| High temperature stability | Stable |
| Low temperature stability | Stable |
| Stability against temperature variation | Stable |
| Stability against high temperature shaking | Stable |
| Texture | A |
| Greasy feel | A |
| Transparent feel | A |
| Compatibility | A |
| Average emulsified particle size (μm) | 0.54 |
| Viscosity (mPa · s) | 6100 |
| pH value | 6.54 |

Example 18

Sun-Block Cream

According to the formulation shown in Table 33, a sun-block cream as an oil-in-water emulsion cosmetic composition was produced.

First, materials (1) to (8) were charged in a 300 ml stainless steel vessel and then mixed and dissolved by disper stirring (1,000 rpm) while heating to 75° C. to obtain an oil phase. Materials (9) to (12) were mixed and dissolved by disper stirring (1,000 rpm) at 70° C. to obtain an aqueous phase. Then, the oil phase at 70° C. was added to the aqueous phase while stirring by a disper stirrer (1,000 rpm) at 70° C.

While continuing homomixer stirring, a material (13) was added, followed by disper stirring for 10 minutes. After cooling to 30° C. while stirring continuously, an oil-in-water emulsion cosmetic composition was taken out. The oil-in-water emulsion cosmetic composition was allowed to stand at 25° C. for 24 hours to obtain 397 g of a sun-block cream as an oil-in-water emulsion cosmetic composition.

With respect to the resulting sun-block cream, stability against temperature, sensory evaluation and physical properties were evaluated. The evaluation results are shown in Table 34. The evaluation was conducted in the same manner as in case of the above-described evaluation of the oil-in-water emulsion cosmetic compositions of Examples 1 to 14.

From the evaluation results, it was confirmed that the sunblock cream of Example 18 is an oil-in-water emulsion cosmetic composition which is excellent in stability and is also excellent in tactile sensation.

TABLE 33

Example 18

| | Material No. | Material | Formulation (% by mass) | Amount (g) |
|---|---|---|---|---|
| Component A | (1) | Polyglycerin fatty acid ester used in Example 3 | 2.1 | 8.4 |
| Component B | (2) | Olive squalane | 11.0 | 44.0 |
| | (3) | Pentaerythritol tetra 2-ethylhexanoate | 6.0 | 24.0 |
| | (4) | 2-ethylhexyl paramethoxycinnamate | 6.0 | 24.0 |
| | (5) | Behenyl alcohol | 1.0 | 4.0 |
| | (6) | Monostearyl glyceryl ether | 1.0 | 4.0 |
| | (7) | Cetanol | 1.0 | 4.0 |
| Component D | (8) | Diglycerin oleic acid ester (Hydroxyl value: 410) | 0.9 | 3.6 |
| | (9) | Methyl paraben | 0.2 | 0.8 |
| | (10) | Glycerin | 4.0 | 16.0 |
| | (11) | 1,3-butylene glycol | 10.0 | 40.0 |
| Component C | (12) | Purified water | 46.8 | 187.2 |
| Thickener (containing component C) | (13) | 3% xanthan gum aqueous solution | 10.0 | 40.0 |
| | | Total | 100.0 | 400.0 |

TABLE 34

| Evaluation items | Example 18 |
|---|---|
| High temperature stability | Stable |
| Low temperature stability | Stable |
| Stability against temperature variation | Stable |
| Stability against high temperature shaking | Stable |
| Texture | A |
| Greasy feel | A |
| Transparent feel | A |
| Compatibility | A |
| Average emulsified particle size (μm) | 0.77 |
| Viscosity (mPa · s) | 58200 |
| pH value | 6.03 |

Example 19

Lotion

According to the formulation shown in Table 35, a lotion as an oil-in-water emulsion cosmetic composition was produced.

First, materials (1) to (4) were charged in a 100 ml stainless steel vessel and then mixed and dissolved by disper stirring (1,000 rpm) while heating to 75° C. to obtain an oil phase. Materials (5) to (8) were mixed and dissolved by disper stirring (1,000 rpm) at 70° C. to obtain an aqueous phase. Then, the oil phase at 70° C. was added to the aqueous phase while stirring by a disper stirrer (1,000 rpm) at 70° C.

While continuing disper stirring for 10 minutes and cooling to 30° C. while stirring continuously, an oil-in-water emulsion cosmetic composition was taken out. The oil-in-water emulsion cosmetic composition was allowed to stand at 25° C. for 24 hours to obtain 499 g of a lotion as an oil-in-water emulsion cosmetic composition.

With respect to the resulting lotion, stability against temperature, sensory evaluation and physical properties were evaluated. The evaluation results are shown in Table 36. The evaluation was conducted in the same manner as in case of the above-described evaluation of the oil-in-water emulsion cosmetic compositions of Examples 1 to 14, but texture and viscosity were not evaluated.

From the evaluation results, it was confirmed that the lotion of Example 19 is an oil-in-water emulsion cosmetic composition which is excellent in stability and is also excellent in tactile sensation.

TABLE 35

Example 19

| | Material No. | Material | Formulation (% by mass) | Amount (g) |
|---|---|---|---|---|
| Component A | (1) | Polyglycerin fatty acid ester used in Example 3 | 0.75 | 3.75 |
| Component B | (2) | Squalane | 0.9 | 4.5 |
| | (3) | Tocopherol acetate | 0.1 | 0.5 |
| Component D | (4) | Diglycerin oleic acid ester (Hydroxyl value: 410) | 0.25 | 1.25 |
| | (5) | Sodium hyaluronate | 1.5 | 7.5 |
| | (6) | 1,3-butylene glycol | 15.0 | 75.0 |
| | (7) | Methyl paraben | 0.1 | 0.5 |
| Component C | (8) | Purified water | 81.4 | 407.0 |
| | | Total | 100.0 | 500.0 |

TABLE 36

| Evaluation items | Example 19 |
|---|---|
| High temperature stability | Stable |
| Low temperature stability | Stable |
| Stability against temperature variation | Stable |
| Stability against high temperature shaking | Stable |
| Texture | — |
| Greasy feel | A |
| Transparent feel | A |
| Compatibility | A |
| Average emulsified particle size (nm) | 45 |
| Viscosity (mPa · s) | — |
| pH value | 6.13 |

Example 20

Cleansing Cream

According to the formulation shown in Table 37, a cleansing cream as an oil-in-water emulsion cosmetic composition was produced.

First, materials (1) to (4) were charged in a 100 ml stainless steel vessel and then mixed and dissolved by disper stirring (1,000 rpm) while heating to 75° C. to obtain an oil phase. Materials (5) and (6) were mixed and dissolved by disper stirring (1,000 rpm) at 70° C. to obtain an aqueous phase. Then, the oil phase at 70° C. was added to the aqueous phase while stirring by a disper stirrer (2,000 rpm) at 70° C.

While continuing disper stirring for 10 minutes and cooling to 30° C. while stirring continuously, an oil-in-water emulsion cosmetic composition was taken out. The oil-in-water emulsion cosmetic composition was allowed to stand at 25° C. for 24 hours to obtain 499 g of a cleansing cream as an oil-in-water emulsion cosmetic composition.

With respect to the resulting cleansing cream, stability against temperature, sensory evaluation and physical properties were evaluated. The evaluation results are shown in Table 38. The evaluation was conducted in the same manner as in case of the above-described evaluation of the oil-in-water emulsion cosmetic compositions of Examples 1 to 14, but sensories, which are not required to the cleansing cream, such as transparent feel and compatibility were not evaluated.

From the evaluation results, it was confirmed that the cleansing cream of Example 20 is an oil-in-water emulsion cosmetic composition which is excellent in stability and tactile sensation, and is also excellent in cleansing ability to cosmetic compositions.

TABLE 37

Example 20

| | Material No. | Material | Amount (g) |
|---|---|---|---|
| Component A | (1) | Polyglycerin fatty acid ester used in Example 2 | 20.0 |
| Component B | (2) | Liquid paraffin | 32.0 |
| | (3) | 2-ethylhexyl palmitate | 20.0 |
| | (4) | Cetanol | 3.0 |
| | (5) | Methyl paraben | 0.2 |
| Component C | (6) | Purified water | 24.8 |
| | | Total | 100.0 |

TABLE 38

| Evaluation items | Example 20 |
|---|---|
| High temperature stability | Stable |
| Low temperature stability | Stable |
| Stability against temperature variation | Stable |
| Stability against high temperature shaking | Stable |
| Texture | A |
| Greasy feel | A |
| Transparent feel | — |
| Compatibility | — |
| Average emulsified particle size (μm) | 0.4 |
| Viscosity (mPa · s) | 6500 |
| pH value | 6.11 |

INDUSTRIAL APPLICABILITY

The oil-in-water emulsion cosmetic composition of the present invention can be used as cream in general, milky lotion, sun tan cream and sun-block cream, shaving cream, cleansing cream, facial cleansing cream, lotion in general, sun tan lotion, and sun-block lotion, shaving lotion, serum, lipstick, gel, cleansing gel, moisture gel, pack, emulsion foundation, emulsified eye shadow, nail treatment, shampoo, conditioner and hair treatment in the filed of cosmetics.

What is claimed is:

1. A method for producing an oil-in-water emulsion cosmetic composition, wherein the oil-in-water emulsion cosmetic composition comprises:

a component A: a polyglycerin fatty acid ester having a hydroxyl value of 450 to 700, a atty acid residue having 16 to 18 carbon atoms accounting for 50 to 100% by mass of all constituent fatty acid residues, the total content of a dimer and a trimer of a cyclic polyglycerin being from 0 to 3% by mass, the total content of an undecamer of polyglycerin being from 10 to 30% by mass, and the each content of a tetramer to a decamer of polyglycerin being from 4 to 20% by mass, based on 100% by mass of polyglycerin constituting the polyglycerin fatty acid ester, a component B: a hydrocarbon oil and/or ester oil, and a component C: water, wherein the amount of the component A is from 0.01% to 15% by mass, the amount of the component B is from 0.01% to 50% by mass, and the amount of the component C is from 30% to 95% by mass, wherein the method comprises the step of adding an oil phase containing the component A and the component B to an aqueous phase containing a component C, and emulsifying the two phases.

2. The method for producing the oil-in-water emulsion cosmetic composition according to claim 1, wherein the emulsifying occurs at a temperature is of 10 to 90° C.

* * * * *

UNITED STATES PATENT AND TRADEMARK OFFICE
CERTIFICATE OF CORRECTION

PATENT NO.         : 8,501,823 B2
APPLICATION NO.    : 12/573667
DATED              : August 6, 2013
INVENTOR(S)        : Jin Fujino et al.

It is certified that error appears in the above-identified patent and that said Letters Patent is hereby corrected as shown below:

Title Page (Item 75) Column 1, Line 5, After Ooyama, change "Kanagawa-ken" to --Yokohama--.

(Item 75) Column 1, Line 6, After Uchida, change "Mie-ken" to --Mie-gun--.

(Item 75) Column 1, Line 7, After Okubo, change "Mie-ken" to --Yokkaichi--.

(Item 56) Column 2, Line 11, Under Other Publications, change "Streitweiser" to --Streitwieser--.

(Item 56) Column 2, Line 16, Under Other Publications, change "PolyglycerinePolyglycerol" to --Polyglycerine Polyglycerol--.

In the Specification

At Column 8, Line 45, Change "isononanate," to --isononanoate,--.

At Column 8, Line 46, Change "isononanate," to --isononanoate,--.

At Column 10, Line 52, Change "acasia," to --acacia,--.

At Column 18, Line 27 (Approx.), Change "TO," to --10,--.

At Column 18, Line 28 (Approx.), Change "T," to --1,--.

Signed and Sealed this
Seventeenth Day of June, 2014

Michelle K. Lee
*Deputy Director of the United States Patent and Trademark Office*

CERTIFICATE OF CORRECTION (continued)
U.S. Pat. No. 8,501,823 B2

At Column 19-20 (Table 6), Line 5 (Approx.), Change "aquesou" to --aqueous--.

At Column 19-20 (Table 8), Line 13 (Approx.), Change "aquesou" to --aqueous--.

At Column 21-22 (Table 10), Lines 14-15 (Approx.), Change

" 
| (containing component C) | 1% by mass sodium hydroxide aqueous solution | 2 | 2 | 2 | |
|---|---|---|---|---|---|
| | Total | 100 | 100 | 100 | 100 |

"

to --

| (containing component C) | 1% by mass sodium hydroxide aqueous solution | 2 | 2 | | 2 |
|---|---|---|---|---|---|
| | Total | 100 | 100 | 100 | 100 |

--.

At Column 21, Line 57, Change "to II" to --to 11--.

At Column 23-24 (Table 11), Line 8 (Approx.), Change "Polylycerin" to --Polyglycerin--.

At Column 23-24 (Table 12), Line 15 (Approx.), Change "aquesou" to --aqueous--.

At Column 25-26 (Table 14), Line 15 (Approx.), Change "aqusou" to --aqueous--.

At Column 27-28 (Table 16), Line 10 (Approx.), Change "aquesou" to --aqueous--.

At Column 35 (Table 29), Line 5 (Approx.), Change "dicaprare" to --dicaprate--.

At Column 36 (Table 31), Line 14 (Approx.), Change "aquesou" to --aqueous--.

At Column 36 (Table 31), Line 16 (Approx.), Change "aquesou" to --aqueous--.

At Column 40, Line 10 (Approx.), Change "filed" to --field--.

In the Claims

At Column 40, Line 17 (Approx.), In Claim 1, change "atty" to --fatty--.

At Column 40, Line 41, In Claim 2, change "is of" to --of--.